United States Patent [19]

Juraszyk et al.

[11] Patent Number: 5,401,722

[45] Date of Patent: Mar. 28, 1995

[54] PEPTIDE ANALOGUES

[76] Inventors: Horst Juraszyk; Peter Raddatz; Johannes Sombroek; Claus J. Schmitges; Klaus-Otto Minck, all of 10 E. Merck, D-6100 Darmstadt, Germany

[21] Appl. No.: 655,581

[22] Filed: Feb. 15, 1991

[30] Foreign Application Priority Data

Feb. 16, 1990 [DE] Germany ............... 40 04 898.5

[51] Int. Cl.⁶ ............... A61K 37/02; C07K 5/08; C07K 5/10
[52] U.S. Cl. .................... 514/18; 514/19; 530/330; 530/331
[58] Field of Search ............. 514/18, 19; 530/330

[56] References Cited

FOREIGN PATENT DOCUMENTS 0296581 12/1988 European Pat. Off. .

OTHER PUBLICATIONS

Burger's Med. Chem. 4th ed. He Wolfee ed (Wiley Interscience)(1981) 288–289.
Burger's Med. Chem. 3rd ed A. Burger ed (Wiley Inter.) (1970) 1021–1052.
Greenlee, *Pharm. Res* vol. 4 (1987) pp. 364–374.
Repyne et al. J. Med. Chem (1991) 34 1935–1943.
Burger, *Med. Chem.* (2nd ed.) Edited by Alfred Burger Jun. 27, 1960 (Interscience Publishers).
Kokubu et al. Biochem. Pharm. vol. 22 (1973) pp. 3217–3223.
Bolts et al. J. Med. Chem 30(10) pp. 1729–1737 (1987).
Plattner et al. J. Med. Chem. 31(12) pp. 2277–2288 (1988).
Fyhrquist et al., "Radioimmunoassay of Plasma Renin Activity", *Clin. Chem.* 22/2, 250–256 (1976).

*Primary Examiner*—Lester L. Lee

[57] ABSTRACT

New peptide analogues of the formula I $$R^1-Z-NR^2-CHR^3-CR^4-(CH_2)_o-(CR^5-)_t-(CH_2)_v-CE-C_wH_{2w}-R^6 \quad I$$

in which $R^1$ to $R^6$ Z, E, o, t and w have the meanings described herein, and the salts thereof, inhibit the activity of human plasma renin.

18 Claims, No Drawings

PEPTIDE ANALOGUES

SUMMARY OF THE INVENTION

The invention relates to new peptide analogues of the formula I

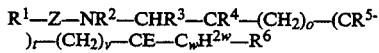

$$R^1-Z-NR^2-CHR^3-CR^4-(CH_2)_o-(CR^5-)_r-(CH_2)_v-CE-C_wH^{2w}-R^6 \quad I$$

in which $R^1$ is H, $R^7-O-C_mH_{2m}-CO-$, $R^7-C_mH_{2m}-O-CO-$, $R^7-C_mH_{2m}-CO-$, $R^7-SO_2-$, $R^8R^9N-C_mH_{2m}-CO-$, $R^{10}-NH-C(=NH)-NH-C_mH_{2m}-CO-$, $R^8OOC-C_mH_{2m}-CO-$, $R^8O_3S-C_mH_{2m}-CO-$ or $R^{11}-C_mH_{2m}-(T)_s-(V)_y-C_nH_{2n}-L(R^7-C_pH_{2p})-C_rH_{2r}-CO-$, Z is 0 to 4 amino acid residues which are linked together in the manner of a peptide and are selected from the group comprising Abu, Ada, Ala, βAla, Arg, Asn, Asp, Bia, Cal, S-A-Cys, Dab, Gln, Glu, Gly, His, N(im)—A—His, Hph, Ile, Isoser, Leu, tert.-Leu, Lys, Mal, Met, Met(O$_2$), αNal, βNal, Nbg, Nle, Nva, Orn, Phe, Pia, Pro, Pya, Ser, Thr, Tia, Tic, Trp, Tyr and Val, wherein one of these radicals may also be replaced by Pla, $R^2$, $R^8$ and $R^9$ are each H or A, $R^3$, $R^7$ and $R^{11}$ are independently each H, A, Ar, Ar-alkyl, Het, Het-alkyl, cycloalkyl having 3–7 C atoms, cycloalkylalkyl having 4–11 C atoms, bicycloalkyl or tricycloalkyl each having 7–14 C atoms, or bicycloalkylalkyl or tricycloalkylalkyl each having 8–18 C atoms, wherein said cycloalkyl, cycloalkylalkyl, bicycloalkyl, tricycloalkyl, bicycloalkylalkyl and tricycloalkylalkyl groups are unsubstituted or substituted singly or multiply by A, AO and/or Hal;

$R^{11}$ is also $R^8O-$, $R^8R^9N-$, $R^8OOC-$ or $A_3N^{\oplus}An^{\ominus}$, $R^4$ is (H, $R^{12}$) or $=O$, and when $R^4$ is (H,$R^{12}$), the $R^{12}$ group of $R^4$ together with $R^2$, can also optionally be the group $-CR^8R^{13}-O-$, $R^5$ is (H, H), (H, OH), (H, OAc), (H, OSiR$^{14}$R$^{15}$R$^{16}$), (H, tetrahydro-2-pyranyloxy) or $=O$, $R^6$ is H, A, CN, CH=Y, COOR$^7$, COR$^7$, CONR$^8$R$^9$, NR$^8$R$^9$, NH—COOR$^7$, NH—COR$^7$, NH—CONR$^8$R$^9$, NH—SO$_2$—R$^7$, NH—SO$_2$NR$^8$R$^9$, OH, OR$^{14}$, OAc, OSO$_2$R$^{14}$, OSiR$^{14}$R$^{15}$R$^{16}$, tetrahydro-2-pyranyloxy, Cl, Br, I, SR$^7$, SOR$^7$ or SO$_2$R$^7$, $R^{10}$ is H, A or CN, $R^{12}$ is OH, OA, NH$_2$, NHAc, OSiR$^{14}$R$^{15}$R$^{16}$ or tetrahydro-2-pyranyloxy, $R^{13}$ is H, A, AR or Ar-alkyl, $R^{14}$, $R^{15}$ and $R^{16}$ are each A or Ar-alkyl, E is $-S(O)_b-CH_2-(CR^{17})_c-CH_2-S(O)_b-$, $R^{17}$ is (H, $R^{12}$), ($R^{13}$, $R^{14}$) or $=O$, L is CH or N, T is O or NR$^{13}$, V is CHOR$^8$, CO, S, SO or SO$_2$, Y is $=O$, $-O-(CH_2)_a-O-$, $-S-(CH_2)_a-S-$ or $-SO_2-(CH_2)_a-SO_2-$, $R^8R^9N$ is also a pyrrolidino, piperidino, morpholino or piperazino group which is unsubstituted or is substituted by A, OH, NH$_2$, NHA, NA$_2$, NHAc, NH—CO—C$_x$H$_{2x}$—O—R$^{16}$, NH—CO—O—C$_x$H$_{2x}$—O—R$^{16}$, hydroxyalkyl, COOH, COOA, CONH$_2$, aminoalkyl, HAN-alkyl, A$_2$N-alkyl, A$_3$N• alkyl An$^{\ominus}$, NH—CO—NH$_2$, NH—CO—NHA, guanidinyl or guanidinylalkyl, a is 2 or 3, b is 0, 1 or 2, c, s, t, v and y are each 0 or 1, m, n, o, p, r, w and x are each 0, 1, 2, 3, 4, 5, 6, 7, 8, 9 or 10, Ar is phenyl which is unsubstituted or is substituted one or more times by A, OA, Hal, CF$_3$, OH, NO$_2$, hydroxyalkyl, NH$_2$, NHA, NA$_2$, NHAc, SA, SO—A, SO$_2$—A, SO$_2$NH$_2$, SO$_2$NHA, COOH, COOA, CONH$_2$, CN, aminoalkyl, HAN-alkyl, A$_2$N-alkyl, A$_3$N• alkyl An$^{\ominus}$ and/or guanidinylalkyl, or is unsubstituted naphthyl, Het is a saturated or unsaturated 5- or 6-membered heterocyclic radical which has 1–4N, O and/or S atoms and can be fused with a benzene ring and/or be substituted one or more times by A, OA, Hal, CF$_3$, OH, NO$_2$, carbonyl oxygen, NH$_2$, NHA, NA$_2$, NHAc, SA, SO—A, SO$_2$—A, SO$_2$NH$_2$, SO$_2$NHA, COOH, COOA, CONH$_2$, CN, NH—SO$_2$—A, Ar, Ar-alkyl, Ar-alkenyl, hydroxyalkyl, aminoalkyl, HAN-alkyl and/or A$_2$N-alkyl, and/or whose N and/or S hetero atoms can also be oxidized, Hal is F, Cl, Br or I, Ac is A—CO—, Ar—CO—, Ar-alkyl—CO—or A—NH—CO—;

An$^{63}$ is an anion, which can also be absent if, in its place, a carboxyl group contained in the compound of the formula I is in the form of a carboxylate anion, -alkyl- is an alkylene group having 1–8 C atoms, and A is alkyl having 1–8 C atoms, in which, furthermore, it is also possible for one or more —NH—CO— groups to be replaced by one or more —NA— CO— groups, as well as the salts thereof.

In the foregoing, selection of variables defined together is made independently.

An object of the invention is to provide new compounds with valuable properties, in particular those which can be used for the preparation of medicaments.

Upon further study of the specification and appended claims, further objects and advantages of this invention will become apparent to those skilled in the art.

It has been found that the compounds of the formula I and the salts thereof have very valuable properties. In particular, they inhibit the activity of human plasma renin. This action can be detected, for example, by the method F. Fyhrquist et al., Clin. Chem. 22, 250–256 (1976). The noteworthy point is that these compounds are very specific inhibitors of renin; as a rule, the concentrations of these compounds necessary for the inhibition of other aspartyl proteinases (for example pepsin and cathepsin D) are about 100 to 1000 times as high as for renin inhibition. The actions of the compounds on the blood pressure and/or on the heart rate, as well as the inhibition of renin activity in blood plasma can furthermore be determined in conscious monkeys, for example, female monkeys (*Macaca fascicularis*); it is possible in this for the blood pressure and heart rate to be measured by a modification of the method of M. J. Wood et al., J. Hypertension 4, 251–254 (1985). In order to stimulate renin activity in this, the animals are preferably pretreated with a saluretic. Blood samples for the determination of the plasma renin activity can be obtained by puncture of the femoral vein.

The compounds can be used as pharmaceutically active substances in human and veterinary medicine, in particular for the prophylaxis and for the treatment of diseases of the heart, circulation and vessels, especially of hypertension, cardiac insufficiency and hyperaldosteronism. In addition, the compounds can be used for diagnostic purposes in order to determine, in patients with hypertension or hyperaldosteronism, the possible contribution of the renin activity to maintaining the pathological state. The procedure for such diagnostic tests can be similar to that indicated in EP-A 77,028 (Apr. 20, 1983).

In addition, the compounds can be employed for the inhibition of the activity of retrovirus proteases. Thus, the compounds can be used for the treatment of retrovirus infections and diseases caused by retroviruses such as acquired immunodeficiency syndrome (AIDS), leukemia and lymphatic cancer. Inhibition of the activity of retrovirus protease can be demonstrated and tested, for example, in accordance with a method by Katoh et al., Nature 329, 654–656 (1987) or Von der Helm et al., Proc. Natl. Acad. Sci. USA, Vol. 85, p. 6612–16 (1988).

The abbreviations quoted hereinbefore and hereinafter for amino acid residues represent the radicals —NR'—R"—CO—, as a rule —NH—CHR—CO— (in which R, R' and R" have the specific meaning known for each amino acid), of the following amino acids:

Abu 2-aminobutyric acid
Ada 3-(1-adamantyl)-alanine
Ala alanine
βAla β-Alanine
Arg arginine
Asn asparagine
Asp aspartic acid
Bia 3-(2-benzimidazolyl)-alanine
Cal 3-cyclohexylalanine
S-A-Cys S-alkyl-cysteine [e.g., S-Me-Cys=S-methyl-cysteine]
Dab 2,4-diaminobutyric acid
Gln glutamine
Glu glutamic acid
Gly glycine
His histidine
N(im)-A-His histidine substituted in the 1 or 3 position of the imidazole ring by A
Hph homophenylalanine (2-amino-4-phenylbutyric acid)
Ile isoleucine
Isoser isoserine (3-amino-2-hydroxypropionic acid)
Leu leucine
tert.-Leu tert.-leucine
Lys lysine
Mal 3-(p-methoxyphenyl)-alanine
Met methionine
Met($O_2$) methionine S,S-dioxide
αNal 3-(α-naphthyl)-alanine
βNal 3-(β-naphthyl)-alanine
Nbg 2-norbornyl-glycine
Nle norleucine
N-Me-His N-methyl-histidine
N-Me-Phe N-methyl-phenylalanine
Nva Norvaline (2-aminovaleric acid)
Orn ornithine
Phe phenylalanine
Pia 3-(piperidyl)-alanine [e.g.,2-Pia=3-(2-piperidyl)-alanine]
Pro proline
Pya 3-(pyridyl)-alanine [e.g., 3-Pya=3-(3-pyridyl)-alanine]
Ser serine
Thr threonine
Tia 3-(thienyl)-alanine [e.g., 2-Tia=3-(2-thienyl)-alanine]
Tic 1,2,3,4-tetrahydroisoquinoline-1-carboxylic acid
Trp tryptophan
Tyr tyrosine
Val valine.

Further meanings hereinafter are:
BOC tert.-butoxycarbonyl
BOM benzyloxymethyl
imi-BOM benzyloxymethyl in the 1 position of the imidazole ring
CBZ benzyloxycarbonyl
DCCI dicyclohexylcarbodiimide
DMF dimethylformamide
DNP 2,4-dinitrophenyl
imi-DNP 2,4-dinitrophenyl in the 1 position of the imidazole ring
ETOC ethoxycarbonyl
FMOC 9- fluorenylmethoxycarbonyl
HOBt 1- hydroxybenzotriazole
IPOC isopropoxycarbonyl
Pla the radical of phenyllactic acid, —O—CH($CH_2C_6H_5$)—CO—(S form)
POA phenoxyacetyl
THF tetrahydrofuran.

If the abovementioned amino acids can occur in several enantiomeric forms, then all these forms, as well as mixtures thereof (for example, the DL-forms), are included hereinbefore and hereinafter, for example as constituents of the compounds of the formula I. The L-forms are preferred. Where individual compounds are mentioned hereinafter, then the abbreviations of these amino acids each relate to the L-form unless expressly indicated otherwise.

The invention furthermore relates to a process for the preparation of a compound of the formula I, and of the salts thereof, characterized in that it is liberated from one of its functional derivatives by treatment with a solvolyzing or hydrogenolyzing agent, or in that a carboxylic acid of the formula II $$R^1—G^1—OH \qquad II$$

in which
G$^1$ is
(a) absent,
(b) Z,
(c) $Z^1$,
or one of the reactive derivatives thereof, is reacted with an amino compound of the formula III $$H—G^2—NR^2—CHR^3—CR^4—(CH_2)_o—(CR^5-)_t—(CH_2)_v—CE—C_wH_{2w}—R^6 \qquad III$$

in which
G$^2$ is
(a) Z,
(b) absent,
(c) $Z^2$ and
$Z^1 + Z^2$ are together Z, or in that, for preparing a compound of the formula I in which b is 0, a carbonyl compound of the formula IV

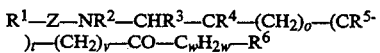   IV is reacted with a dithiol of the formula V $$HS-CH_2-(CR^{17})_c-CH_2-SH \quad V$$

or with one of its salts, or in that, for preparing a compound of the formula I in which E is —SO$_2$—CH$_2$—(CR$^{17}$)$_c$—CH$_2$—SO$_2$—, a compound of the formula VI

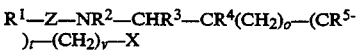   VI in which
X is Cl, Br, I or an OH group which is esterified in a reactive way,
is reacted with a compound of the formula VII

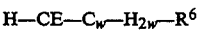   VII and in that where appropriate, a compound of the formula I is converted into another compound of the formula I, and/or a compound of the formula I is converted by treatment with an acid or base into one of the salts thereof.

Hereinbefore and hereinafter the radicals and parameters R$^1$ to R$^{17}$, Z, E, L, T, V, X, Y, a, b, c, m, n, o, p, r, s, t, v, w, x, y, At, Het, Hal, Ac, An$^\ominus$, A, G$^1$, G$^2$, Z$^1$ and Z$^2$ have the meanings indicated for the formulae I, II or III unless expressly indicated otherwise, A in the abovementioned formulae has 1-8, preferably 1, 2, 3 or 4 C atoms. A is preferably methyl, furthermore ethyl, propyl, isopropyl, butyl, isobutyl, sec.-butyl or tert.-butyl, as well as pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl.

Typically, all "alkyl" and "alkenyl" portions mentioned above have up to 8 C atoms, including, for example, the alkylene and alkenylene portions of Ar-alkenyl, Ar-alkyl, guanidinyl-alkyl, HAN-alkyl, A$_2$N-alkyl, and A$_3$N$^\oplus$ alkyl An$^\ominus$.

Cycloalkyl is preferably cyclopropyl, cyclobutyl, cyclopentyl, cyclohexyl or cycloheptyl, but is also, for example, 1-, 2- or 3-methylcyclopentyl, or 1-, 2-, 3- or 4-methylcyclohexyl.

Correspondingly, cycloalkylalkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl, but is also, for example, 1-, 2- or 3-methylcyclopentylmethyl, or 1-, 2-, 3- or 4-methylcyclohexylmethyl.

Bicycloalkyl is preferably 1-or 2-decalyl, 2-bicyclo[2.2.1]heptyl or 6,6-dimethyl-2-bicyclo[3.1.1]heptyl.

Tricycloalkyl is preferably 1-adamantyl.

Hal is preferably F, Cl or Br, but is also I.

Ac is preferably A—CO—, such as acetyl, propionyl or butyryl, Ar—CO— such as benzoyl, o-, m- or p-methoxybenzoyl or 3,4-dimethoxybenzoyl, or A—N-H—CO—such as N-methyl- or N-ethylcarbamoyl.

Ar is preferably phenyl and is furthermore preferably o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, o-, m- or p-hydroxyphenyl, o-, m- or p-sulfamoylphenyl, 2,3-, 2,4-, 2,5-, 2,6-, 3,4- or 3,5-dimethoxyphenyl, 3,4,5-trimethoxyphenyl, o-, m- or p-aminophenyl, o-, m- or p-aminomethylphenyl, o-, m- or p-dimethylaminomethylphenyl, o-, m- or p-guanidinomethylphenyl, or 1- or 2-naphthyl.

Correspondingly, Ar-alkyl is preferably benzyl, 1- or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxybenzyl, 1- or 2-o-, -m- or -p-methoxyphenylethyl, o-, m- or p-fluorobenzyl, 1- or 2-o-, -m- or -p-fluorophenylethyl, o-, m- or p-chlorobenzyl, 1- or 2 -o-, -m- or -p-chlorophenylethyl, o-, m- or p-bromobenzyl, 1- or 2-o-, -m- or -p-bromophenylethyl, o-, m- or p-iodobenzyl, 1- or 2-o-, -m- or -p-iodophenylethyl, o-, m- or p-trifluoromethylbenzyl, o-, m- or p-hydroxybenzyl, 2,3-, 2,4-, 2,5-, 2,6,3,4- or 3,5-dimethoxybenzyl, 3,4,5-trimethoxybenzyl, o-, m- or p-aminobenzyl, o-, m- or p-aminomethylbenzyl, o-, m- or p-dimethylaminomethylbenzyl, o-, m- or p-guanidinomethylbenzyl, or 1-or 2-naphthylmethyl.

Het is preferably 2- or 3-furyl, 2- or 3-thienyl, 1-, 2- or 3-pyrrolyl, 1-, 2-, 4- or 5-imidazolyl, 1-, 3-, 4 - or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-l-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or 5-yl, 2,1,5-thiadiazol-3-or-4-yl, 2-, 3-, 4-, 5-or 6-2H-thiopyranyl, 2-, 3-or 4-4H-thiopyranyl, 3-or 4-pyridazinyl, pyrazinyl, 2-, 3-, 4-, 5-, 6-or 7-benzofuryl, 2-, 3-, 4-, 5-, 6-.or 7-benzothienyl, 1-, 2-, 3-, 4-, 5-, 6- or 7 -indolyl, 1-, 2-, 3-, 4-, 5-, 6- or 7-isoindolyl, 1-, 2 -, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7- benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7-or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8-or 9-acridinyl, 3-, 4-, 5-, 6-, 7- or 8-cinnolyl, 2-, 4-, 5-, 6-, 7- or 8-quinazolyl. The heterocyclic radicals can also be partially or completely hydrogenated. Thus, Het can also be, for example, 2,3-dihydro-2-, -3-, -4- or -5-furyl, 2,5-dihydro-2-, -3-, -4- or -5-furyl, tetrahydro-2- or -3-furyl, tetrahydro-2-or-3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-l, -2-, -3-, -4-, -5-, -6-, -7 - or -8-quinolyl, 1,2,3,4-tetrahydro-1-, -2 -, -3-, -4 -, -5-, -6-, -7 - or -8-isoquinolyl.

The heterocyclic radicals can also be substituted as indicated. Het can also preferably be, for example, 2-amino-4-thiazolyl, 4-carboxy-2-thiazolyl, 4-carbamoyl-2thiazolyl, 4-( 2-aminoethyl)-2-thiazolyl, 4-amino-2-methyl-5-pyrimidinyl, 2-amino-5,6-dimethyl-3-pyrazinyl, 4-carbamoylpiperidino, furthermore, for example, 3-, 4or 5-methyl-2-furyl, 2-, 4- or 5-methyl-3-furyl, 2,4-dimethyl-3-furyl, 5-nitro-2-furyl, 5-styryl-2-furyl, 3-, 4- o 5-methyl-2-thienyl, 2-, 4- or 5-methyl-3-thienyl, 3-methyl-5-tert.-butyl-2-thienyl, 5-chloro-2-thienyl, 5-phenyl-2- or -3-thienyl, 1-, 3-, 4- or 5-methyl-2-pyrrolyl, 1-methyl-4- or -5-nitro-2-pyrrolyl, 3,5-dimethyl-4-ethyl-2-pyrrolyl, 4-methyl-5-pyrazolyl, 5-methyl-3-isoxazolyl, 3,4-dimethyl-5-isoxazolyl, 4- or 5-methyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl-2-pyridyl, 2-, 4-, 5-or 6-methyl-3-pyridyl, 2- or 3-methyl-4-pyridyl, 3-, 4-, 5- or 6-chloro-2-pyridyl, 2-, 4-, 5- or 6-chloro-3-pyridyl, 2- or 3-chloro-4-pyridyl, 2,6-dichloropyridyl, 2-hydroxy-3-, -4-, -5- or -6-pyridyl(-1H-2-pyridon-3-, -4-, -5- or -6-yl), 5-phenyl- 1H-2-pyridon-3-yl, 5-p-methoxyphenyl-1H-2-pyridon-3-yl, 2-methyl-3-hydroxy-4-hydroxymethyl-5-pyridyl, 2-hydroxy-4-amino-6-methyl-3-pyridyl, 3-N'-methylureido- 1H-4-pyridon-5-yl, 4-methyl-2-pyrimidinyl, 4,6-dimethyl-2-pyrimidinyl, 2-, 5 - or 6 -methyl-4-pyrimidinyl, 2,6-dimethyl-4-pyrimidinyl, 2,6-dihydroxy-4-pyrimidinyl, 5-chloro-2-methyl-4-pyrimidinyl, 3-methyl-2-benzofuryl, 2-ethyl-3-benzofuryl, 7-methyl-2-benzothienyl, 1-, 2-, 4-, 5-, 6- or 7-methyl-3-indolyl, 1-methyl-5- or -6-benzimidazolyl, 1-ethyl-5-or-6-benzimidazolyl, 3-, 4-, 5-, 6-, 7-or 8-hydroxy-2-quinolyl, 2-oxo-pyrrolidino, 2-oxo-piperidino, 2,5-dioxopyrrolidino or 3-benzyl-2,5-dioxopyrrolidino.

$R^1$ is, in general, preferably $R^8R^9N$—$C_mH_{2m}$—CO— or $R^{11}$—$C_mH_{2m}$—$(T)_s$—$(V)_y$—$C_nH_{2n}$—L(-$R^7$—$C_pH_{2O}$)—$C_rH_{2r}$—CO—, furthermore preferably $R^7$—$C_mH_{2m}$—O—CO—, $R^7$—$C_mH_{2m}$—CO— or $R^8$OOC—$C_mH_{2m}$—CO—.

The group Z preferably consists of zero, one or two of the stated amino acid residues; however, it can also contain three or four amino acid residues. Z is preferably His or Phe-His, furthermore preferably βAla, Gly, Ils, Leu, Mal, Nle, Nva, Phe, Val, Mal-βAla, Mal-Gly, Mal-His, Mal-Ile, Mal-Leu, Mal-Nle, Mal-Nva, Mal-Val, αNal-His, βNal-His, Phe-Abu, Phe-Ala, Phe-βAla, Phe-Ash, Phe-Gln, Phe-Glu, Phe-Gly, Phe-Ile, Phe-Leu, Phe-Nle, Phe-Nva, Phe-Pya (especially Phe-3-Pya), Phe-Tia (especially Phe-3-Tia), Phe-Val, Pro-Phe Tia-His (especially 3-Tia-His ), Trp-His, Pro-Phe-βAla, Pro-Phe-Gly, Tyr-His, Pro-Phe-His or Pro-Phe-N-Me-His.

$R^2$, $R^6$, $R^8$, $R^9$ and $R^{13}$ are each preferably H and furthermore preferably methyl; $R^6$ is also preferably COOA, in particular COOCH$_3$ or COOC$_2$H$_5$. $R^6R^9N$ is also preferably pyrrolidino, piperidino, morpholino, amino-piperidino such as 4-aminopiperidino, alkylaminopiperidino such as 4-methylaminopiperidino, or dialkylaminopiperidino such as 4-dimethylaminopiperidino.

$R^3$ is preferably cycloalkylalkyl, especially cyclohexylmethyl, furthermore preferably alkyl, especially isobutyl; Ar-alkyl, especially benzyl; cycloalkyl, especially cyclohexyl.

$R^4$ is preferably (H, OH).

$R^5$ is preferably (H, H).

$R^7$ is preferably A, especially methyl, ethyl, isopropyl or tert.-butyl; or Ar, especially phenyl, 1- or 2-naphthyl.

$R^{10}$ is preferably H, methyl or CN.

$R^{11}$ is preferably H; A, especially methyl or tert.-butyl; $R^8R^9N$, especially A$_2$N such as (CH$_3$)$_2$N, piperidino or 4-aminopiperidino.

$R^{12}$ is preferably OH. If $R^2$ and $R^{12}$ together are —CR$^8$R$^{13}$—O—, $R^8$ and $R^{13}$ are each preferably A, especially methyl.

$R^{14}$ is preferably A, especially methyl, ethyl, propyl, isopropyl, butyl, isobutyl, sec.-butyl, tert.-butyl, pentyl or isopentyl; or Ar-alkyi, especially benzyl.

$R^{15}$ and $R^{16}$ are preferably A, especially methyl, isopropyl or tert.-butyl; or Ar-alkyl, especially benzyl.

$R^{17}$ is preferably (H, H).

E is preferably —S—(CH$_2$)$_3$—S— or SO$_2$—(CH$_2$)$_3$—SO$_2$—.

L is preferably: CH, furthermore preferably N.

T is preferably O or NH.

V is preferably CO or SO$_2$.

The parameter a is preferably 2; b is preferably 2, furthermore preferably 0; c is preferably 1; o is preferably 0; t is preferably 1; v, w and x are each preferably 0, furthermore preferably 1; s is preferably 0, but also 1; y is preferably 1 but also 0. The sum s+y is preferably I but also 0 or 2. The parameter m is preferably 1, 2 , 3, 4 or 5; n is preferably 1; p is preferably 1; r is preferably I or 0. The groups C$_m$H$_{2m}$, C$_n$H$_{2n}$, C$_p$H$_{2p}$ and C$_r$H$_{2r}$ are preferably straight-chain and thus are preferably —(CH$_2$)$_m$—, —(CH$_2$)$_n$—, —(CH$_2$)$_p$— or —(CH$_2$)$_r$—.

Accordingly, the group $R^1$ is preferably $R^8R^9N$—(CH$_2$)$_m$—CO—, especially H$_2$N—C$_m$H$_{2m}$—CO— such as aminocarbonyl, aminoacetyl (H-Gly-)-, 3-aminopropionyl (H-βAla-), 4-aminobutyryl, 5-aminopentanoyl, 6-aminohexanoyl, 7-aminoheptanoyl, 8-aminooctanoyl, 9-aminononanoyl, 10-aminodecanoyl, 11-aminoundecanoyl, but also, for example, 2-aminopropionyl (Ala), 2-amino-2-methylpropionyl; AN H—C$_m$H$_{2m}$—CO— such as methylaminocarbonyl, methylaminoacetyl (sarcosyl), 3-methylaminopropionyl, 4-methylaminobutyryl, 5-methylaminopentanoyl, 6-methylaminohexanoyl, 6-ethylaminohexanoyl, 7-methylaminoheptanoyl, 8-methylaminooctanoyl, 9-methylaminononanoyl, 10-methylaminodecanoyl, 11-methylaminoundecanoyl; A$_2$N—C$_m$H$_{2m}$—CO— such as dimethylaminocarbonyl, dimethylaminoacetyl, 3-dimethylaminopropionyl, 4-dimethylaminobutyryl, 5-dimethylaminopentanoyl, 6-dimethylaminohexanoyl, 6-diethylaminohexanoyl, 7-dimethylaminoheptanoyl, 8-dimethylaminooctanoyl, 9-dimethylaminononanoyl, 10-dimethylaminodecanoyl, 11-dimethylaminoundecanoyl; A—O—CO—NH—C$_m$H$_{2m}$—CO— such as BOC-Gly, ETOC-Gly, IPOC-Gly, BOC-βAla, ETOC-βAla, IPOC-βAla, 4-BOC-amino-butyryl, 5-BOC-amino-pentanoyl, 6-BOC-amino-hexanoyl, 7-BOC-amino-heptanoyl, 8-BOC-amino-octanoyl, 9-BOC-amino-nonanoyl, 10-BOC-amino-decanoyl, 11-BOC-amino-undecanoyl; ArCH$_2$—O—CO—NH—C$_m$H$_{2m}$—CO— such as CBZ-Gly-, CBZ-βAla, 4-CBZ-amino-butyryl, 5-CBZ-amino-hexanoyl, 7-CBZ-amino-heptanoyl, 8-CBZ-amino-octanoyl, 9-CBZ-amino-nonanoyl, 10-CBZ-amino-decanoyl, 11 -CBZ -amino-undecanoyl; pyrrolidino-C$_m$H$_{2m}$—CO— such as pyrrolidinocarbonyl, pyrrolidino-acetyl, 3-pyrrolidino-propionyl, 4-pyrrolidino-butyryl, 5-pyrrolidino-pentanoyl, 6-pyrrolidino-hexanoyl, 7-pyrrolidino-heptanoyl, 8-pyrrolidino-octanoyl, 9-pyrrolidinononaneyl, 10-pyrrolidino-decanoyl; piperidino-C$_m$H$_{2m}$—CO— such as piperidinocarbonyl, piperidinoacetyl, 3-piperidino-propionyl, 4-piperidino-butyryl, 5-piperidinopentanoyl, 6-piperidino-hexanoyl, 7-piperidino-heptanoyl, 8-piperidino-octanoyl, 9-piperidino-nonanoyl, 10-piperidino-decanoyl; morpholino-C$_m$H$_{2m}$—CO— such as morpholinocarbonyl, morpholinoacetyl, 3-morpholino-propionyl, 4-morpholino-butyryl, 5-morpholino-pentanoyl, 6-morpholino-hexanoyl, 7-morpholino-heptanoyl, 8-morpholino-octanoyl, 9-morpholino-nonanoyl, 10-morpholino-decanoyl; 4-amino-piperidino-$C_mH_{2m}$—CO— such as 4-amino-piperidino-carbonyl, 4-amino-piperidino-acetyl, 3-(4-amino-piperidino)propionyl, 4-(4-amino-piperidino)-butyryl, 5-(4-aminopiperidino)-pentanoyl, 6-(4-amino-piperidino)-hexanoyl, 7-(4-amino-piperidino)-heptanoyl, 8-(4-aminopiperidino)-octanoyl, 9-(4-amino-piperidino)-nonanoyl, 10-(4-amino-piperidino)-decanoyl; 4-dialkylamino-piperidino-$C_mH_{2m}$—CO— such as 4-dimethylamino-piperidinocarbonyl, 4-dimethylamino-piperidino-acetyl; 4-guanidino-piperidino-$C_mH_{2m}$—CO— such as 4-guanidino-piperidino-carbonyl, 4-guanidino-piperidino-acetyl; 4-carboxy-piperidino-$C_mH_{2m}$—CO— such as 4-carboxy-piperidino-carbonyl, 4-carboxy-piperidino-acetyl; 4-alkoxycarbonyl-piperidino-$C_mH_{2m}$—CO— such as 4-methoxycarbonyl-piperidino-carbonyl, 4-ethoxy-carbonyl-piperidino-carbonyl, 4-methoxycarbonyl-piperidino-acetyl, 4-ethoxycarbonyl-piperidino-acetyl; 4-AcNH-piperidino-$C_mH_{2m}$—CO— such as 4-acetamido-piperidinocarbonyl, 4-acetamido-piperidino-acetyl; $H_2N$—C(=NH)—NH—$C_mH_{2m}$—CO— such as guanidinoacetyl, 3-guanidino-propionyl, 4-guanidino-butyryl, 5-guanidino-pentanoyl, 6-guanidinohexanoyl, 7-guanidino-heptanoyl, 8-guanidino-octanoyl; NC—NH—C(=NH)—NH—$C_mH_{2m}$—CO— such as N'-cyanoguanidinoacetyl, 3-(N'-cyanoguanidino)-propionyl, 4-(N'-cyanoguanidino)-butyryl, 5-(N'-cyanoguanidino)-pentanoyl, 6-(N'-cyanoguanidino)-hexanoyl, 7-(N'-cyanoguanidino)heptanoyl, 8-(N'-cyanoguanidino)-octanoyl; HOOC—$C_mH_{2m}$—CO— such as malonyl, succinyl, glutaryl, adipyl, 6-carboxyhexanoyl, 7-carboxy-heptanoyl, 8-carboxyoctanoyl, 9carboxynonanoyl, 10-carboxy-decanoyl, 11-carboxyundecanoyl; AOOC-$C_mH_{2m}$—CO— such as methoxycarbonyl-acetyl, 3-methoxycarbonyl-propionyl, 4-methoxycarbonyl-butyryl, 5-methoxycarbonyl-pentanoyl, 6-methoxycarbonyl-hexanoyl, 7-methoxycarbonyl-heptanoyl, 8-methoxycarbonyl-octanoyl, 9-methoxycarbonyl-nonanoyl, 10-methoxycarbonyl-decanoyl, ethoxycarbonyl-acetyl, 3-ethoxycarbonyl-propionyl, 4-ethoxycarbonyl-butyryl, 5-ethoxycarbonyl-pentanoyl, 6-ethoxycarbonyl-hexanoyl, 7-ethoxycarbonyl-heptanoyl, 8-ethoxycarbonyl-octanoyl, 9-ethoxycarbonyl-nonanoyl, 10-ethoxycarbonyl-decanoyl; H—$SO_3$—$C_mH_{2m}$—CO— such as sulfoacetyl, 3-sulfo-propionyl, 4-sulfo-butyryl, 5-sulfopentanoyl, 6-sulfo-hexanoyl, 7-sulfo-heptanoyl, 8-sulfooctanoyl, 9-sulfo-nonanoyl, 10-sulfo-decanoyl; A-$SO_3$-$C_mH_{2m}$—CO— such as methoxysulfonyl-acetyl, 3-methoxysulfonyl-propionyl, 4-methoxysulfonyl-butyryl, 5-methoxysulfonyl-pentanoyl, 6-methoxysulfonyl-hexanoyl, 7-methoxysulfonyl-heptanoyl, 8-methoxysulfonyl-octanoyl, 9-methoxysulfonyl-nonanoyl, 10-methoxysulfonyl-decanoyl, ethoxysulfonyl-acetyl, 3-ethoxysulfonyl-propionyl, 4-ethoxysulfonyl-butyryl, 5-ethoxysulfonyl-pentanoyl, 6-ethoxysulfonyl-hexanoyl, 7-ethoxysulfonyl-heptanoyl, 8-ethoxysulfonyl-octanoyl, 9-ethoxysulfonyl-nonanoyl, 10-ethoxysulfonyl-decanoyl; $R^{11}$—$C_mH_{2m}$—CO—$C_nH_{2m}$—CH($R^7$—$C_pH_{2p}$)—$C_rH_{2r}$—CO— especially A—CO—$CH_2$—CH(Ar—$CH_2$)—CO— such as 2-benzyl-4-oxo-5,5-dimethylhexanoyl, 2-(1-naphthylmethyl)-4-oxo-5,5-dimethyl-hexanoyl; furthermore $R^8R^9N$—CO—$CH_2$—CH(Ar—$CH_2$)—CO— such as 2-benzyl-3-(4-aminopiperidinocarbonyl)-propionyl, 2-(1-naphthylmethyl)-3-(4-aminopiperidinocarbonyl)-propionyl; $R^{11}$—$C_m$—$H_{2m}$—$SO_2$—$C_nH_{2n}$—CH(-$R^7$—$C_pH_{2p}$)—$C_rH_{2r}$—CO—, especially $R^8R^9N$—($CH_2$)$_m$—NH—CO—$CH_2$—CH(Ar—$CH_2$)—CO— such as 2-benzyl-3-tert.-butylsulfonylpropionyl, 2-(1-naphthylmethyl)-3-tert.-butylsulfonylpropionyl; $R^{11}$—$C_mH_{2m}$—NH—CO—$C_nH_{2n}$—CH($R^7$—$C_pH_{wp}$)—$C_rH_{2r}$—CO—, especially $R^8R^9N$—($CH_2$)$_m$—NH—CO—$CH_2$—CH(Ar—$CH_2$)—CO— such as 2-benzyl-3-(N-3-dimethylaminopropyl-carbamoyl)-propionyl, 2-(1-naphthylmethyl)-3-(N-3-dimethylaminopropyl-carbamoyl)-propionyl, 2-benzyl-3-(N-5-dimethylaminopentyl-carbamoyl)-propionyl; A-CH ($R^7$-$C_pH_{2p}$)—$C_rH_{2r}$—CO—, especially A—CH(Ar—$CH_2$)—CO— such as 2-benzylhexanoyl, 2-benzyl-heptanoyl; $R^{11}$—$C_mH_{2m}$—NH—CO—, especially $R^8R^9N$—($CH_2$)$_m$—NH—CO— such as N-3-dimethylaminopropyl-carbamoyl, N-5-dimethylaminopentyl-carbamoyl; $R^{11}$—$C_mH_{2m}$—N($R^7$—$C_pH_{20}$)—$C_rH_{2r}$—CO—, especially A—N(Ar—$CH_2$)—CO— such as N-benzyl-N-butyl-carbamoyl, N-benzyl-N-isopentyl-carbamoyl; $R^7$—$C_mH_{2m}$—O—CO— especially A—O—CO— such as ETOC, IPOC, BOC as well as Ar—$C_mH_{2m}$—O—CO— such as CBZ; $R^7$—$C_mH_{2m}$—CO— such as 3,3-dimethylbutyryl.

The compounds of the formula I may have one or more chiral centers and therefore exist in various, optically active or optically inactive, forms. The formula I embraces all these forms. If $R^3$ is different from H and-/or $R^4$ is different from =O the enantiomers' with the S configuration at these chiral centers are preferred.

The abovementioned cyclic groups, especially the cycloalkyl and phenyl groups, are preferably unsubstituted or carry preferably 1 to 3, especially 1 or 2, substituents.

Accordingly, the invention particularly relates to those compounds of the formula I in which at least one of the said radicals has one of the preferred meanings indicated hereinbefore. Some preferred groups of compounds can be represented by the following part-formulae Ia to Ik:

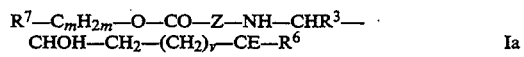  Ia

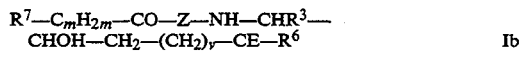  Ib

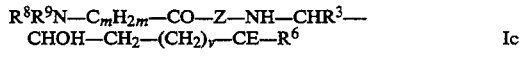  Ic

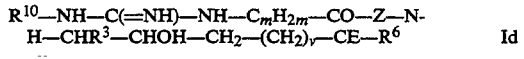  Id

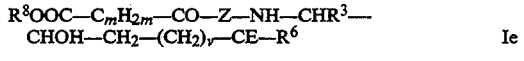  Ie

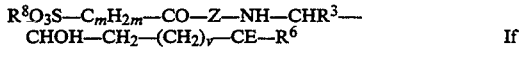  If

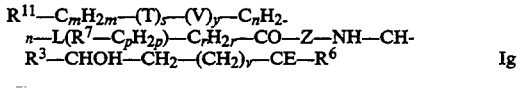  Ig

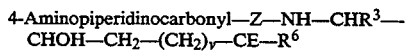

4-Aminopiperidinocarbonyl—Z—NH—CHR³—CHOH—CH₂—(CH₂)ᵥ—CE—R⁶  Ih

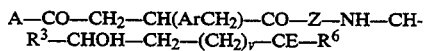

A—CO—CH₂—CH(ArCH₂)—CO—Z—NH—CH-R³—CHOH—CH₂—(CH₂)ᵥ—CE—R⁶  Ii

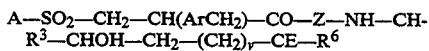

A—SO₂—CH₂—CH(ArCH₂)—CO—Z—NH—CH-R³—CHOH—CH₂—(CH₂)ᵥ—CE—R⁶  Ij

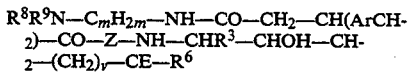

R⁸R⁹N—CₘH₂ₘ—NH—CO—CH₂—CH(ArCH₂)—CO—Z—NH—CHR³—CHOH—CH₂—(CH₂)ᵥ—CE—R⁶  Ik

Particularly preferred are compounds of the part-formulae:

(a) Iaa to Ika, which correspond to the formulae Ia to Ik but in which additionally
Z is absent or is His, Leu, Mal-His, Phe-His or Phe-Leu;

(b) Iab to Ikb and Iaab to Ikab, which correspond to the formulae Ia to Ik and Iaa to Ika but in which additionally
R³ is isobutyl or cyclohexylmethyl;

(c) Iac to Ikc and Iaac to Ikac, which correspond to the formulae Ia to Ik and Iaa to Ika but in which additionally
R³ is cyclohexylmethyl.

Especially preferred are compounds of the part-formulae:

I* and Ia* to Ik*, which correspond to the formulae I and Ia to Ik, as well as those compounds which correspond to the other abovementioned part-formulae but in which additionally
E is —S—(CH₂)₃—S— or —SO₂—(CH₂)₃—SO₂—;

I' and Ia' to Ik', which correspond to the formulae I and Ia to Ik, as well as those compounds which correspond to the other abovementioned part-formulae but in which additionally
v is 0 and/or
R⁶ is H.

A selected group of preferred compounds corresponds to the formula I in which
R¹ is H, BOC, 4-BOC-amino-piperidinocarbonyl, 4-aminopiperidinocarbonyl, 3-BOC-amino-3-methylbutyryl, 3-amino-3-methylbutyryl, 2-benzyl-3-tert.-butylsulfonyl-propionyl or phenylcarbamoyl,
Z is absent or is His, Leu, Mal-His, Phe-His or Phe-Leu,
R³ is cyclohexylmethyl,
R⁴ is (H, OH),
o and w are each 0,
t is 1,
R⁵ is (H, H),
v is 0 or 1,
E is —S—(CH₂)₃—S— or —SO₂—(CH₂)₃—SO₂— and
R⁶ is H or CH₃.

Particularly preferred compounds of the formula I are those in which
R¹ is BOC, 4-BOC-amino-piperidinocarbonyl or 4-aminopiperidinocarbonyl,
Z is Phe-His or Phe-Leu,
R³ is cyclohexylmethyl,
R⁴ is (H, OH),
o, v and w are each 0,
t is 1,
R⁵ is (H, H),
E is —SO₂—(CH₂)₃—SO₂— and
R⁶ is H.

The compounds of the formula I, as well as the starting materials for the preparation thereof, are furthermore prepared by methods which are known per se and as are described in the literature (for example in the standard works such as Houben-Weyl, Methoden der organischen Chemie (Methods of Organic Chemistry), published by Georg Thieme, Stuttgart; as well as EP-A 45665 (Feb. 10, 1982), EP-A 77028 (Apr. 20, 1983), EP-A 77029 (Apr. 20, 1983), EP-A 81783 (Jun. 22, 1983) and EP-A 249096 (Dec. 16, 1987), specifically under reaction conditions which are known and suitable for the said reactions. In this connection it is also possible to make use of variants which are known per se and which are not mentioned in detail herein.

It is also possible, if desired, to form the starting materials in situ so that they are not isolated from the reaction mixture but are immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which correspond to the formula I apart from containing, in place of one or more free amino and/or hydroxyl groups, corresponding protected amino and/or hydroxyl groups, preferably those which carry an amino protective group in place of an H atom bonded to an N atom, for example those which correspond to the formula I but contain in place of an His group an N(im)-R'-His group (in which R' is an amino protective group, for example BOM or DNP).

Further preferred starting materials are those which carry, in place of the H atom of a hydroxyl group, a hydroxyl protective group, for example those of the formula R¹—Z—NR²—CHR³—CHOR''—(CH₂)ₒ—(CR⁵)ₜ—(CH₂)ᵥ—CE—CwH₂w—R⁶ in which R'' is a hydroxyl protective group.

It is also possible for more than one—identical or different—protected amino and/or hydroxyl groups to be present in the molecule of the starting material. If the protective groups which are present differ from one another it is also possible to eliminate them selectively.

The term "amino protective group" is generally known and relates to groups which are suitable for protecting (blocking) an amino group from chemical reactions but which can easily be removed after the desired chemical reaction has been carried out elsewhere in the molecule. Typical of such groups are, in particular, unsubstituted or substituted acyl, aryl (for example DNP), aralkoxymethyl (for example BOM) or aralkyl groups (for example benzyl, 4-nitrobenzyl, triphenylmethyl). Since the amino protective groups are removed after the desired reaction (or reaction sequence), their nature and size are not otherwise critical; however, those which are preferred have 1-20, in particular 1-8, C atoms. The term "acyl group" in connection with the present process is to be interpreted in the widest sense. It embraces acyl groups derived from aliphatic, araliphatic, aromatic or heterocyclic carboxylic acids or sulfonic acids, as well as, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ETOC, 2,2,2-trichloroethoxycarbonyl, IPOC, BOC, 2-iodoethoxycarbonyl; aralkyloxycarbonyl such as CBZ, 4-methoxybenzyloxycarbonyl, FMOC. Preferred amino protective groups are BOC, DNP and BOM, as well as CBZ, FMOC, benzyl and acetyl.

The term "hydroxyl protective group" is likewise generally known and relates to groups which are suitable for protecting a hydroxyl group from chemical reactions but which can easily be removed after the desired chemical reaction has been carried out elsewhere in the molecule. Typical of such groups are the abovementioned unsubstituted or substituted aryl, aralkyl or acyl groups, as well as alkyl groups. The nature and size of the hydroxyl protective groups is not critical because they are removed again after the desired chemical reaction or reaction sequence; preferred groups have 1-20 especially 1-10, C atoms. Examples of hydroxyl protective groups are, inter alia, tert.-butyl, benzyl, p-nitrobenzoyl, p-toluenesulfonyl and acetyl, with benzyl and acetyl being particularly preferred.

The functional derivatives of the compounds of the formula I which are to be used as starting materials can be prepared by customary methods of amino acid and peptide synthesis as are described, for example, in the said standard works and patent applications, for example also by the solid-phase method of Merrifield.

The liberation of the compounds of the formula I from their functional derivatives is effected—depending on the protective group used—for example with strong acids, preferably with trifluoroacetic acid or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary. Suitable and preferred inert solvents are organic, for example carboxylic acids such as acetic acid, ethers such as tetrahydrofuran or dioxane, amides such as dimethylformamide (DMF), halogenated hydrocarbons such as dichloromethane, as well as alcohols such as methanol, ethanol or isopropanol, and water. Furthermore suitable are mixtures of the abovementioned solvents. Trifluoroacetic acid is preferably used in excess without the addition of another solvent, and perchloric acid in the form of a mixture of acetic acid and 70% perchloric acid in the ratio 9:1. The reaction temperatures for the cleavage are preferably between about 0° and about 50°, especially between 15° and 30° (room temperature).

The BOC group can be eliminated, for example, preferably with 40% trifluoroacetic acid in dichloromethane or with about 3 to 5 N HCl in ethyl acetate or dioxane at 15°–30°, and the FMOC group with an approximately 5–20% solution of dimethylamine, diethylamine or piperidine in DMF at 15°–30°. Elimination of the DNP group is effected, for example, also with an approximately 3–10% solution of 2-mercaptoethanol in DMF/water at 15°–30°.

Protective groups which can be removed by hydrogenolysis (for example BOM, CBZ or benzyl) can be eliminated, for example by treatment with hydrogen in the presence of a catalyst (for example a noble metal catalyst such as palladium, preferably on a support such as carbon). Solvents suitable for this are those mentioned above, especially, for example, alcohols such as methanol or ethanol or amides such as DMF. Hydrogenolysis is, as a rule, carried out at temperatures between about 0° and 100° under pressures between about 1 and 200 bar, preferably at 20°–30° and under 1–10 bar. Hydrogenolysis of the CBZ group is effected satisfactorily, for example, on 5–10% Pd-C in methanol at 20°–30°.

Compounds of the formula I can also be obtained by direct peptide synthesis from a carboxylic acid component (formula II) and an amine component (formula III). Examples of suitable carboxylic acid components are those of the part-formulae (a) $R^1$—OH, (b) $R^1$—Z—OH, and of amine components are those of the part-formulae (a) H—Z—$NR^2$—$CHR^3$—$CR^4$—$(CH_2)_o$—$(CR^5)_t$—$(CH_2)_v$—CE—$C_wH_{2w}$—$R^6$, (b) H—$NR^2$—$CHR^3$—$CR^4$—$(CH_2)_o$—$(CR^5)_t$—$(CH_2)_v$—CE—$C_wH_{2w}$—$R^6$. The peptide linkage can, however, also be formed within the group Z; this entails a carboxylic acid of the formula $R^1$—$Z^1$—OH being reacted with an amino compound of the formula H—$Z^2$—$NR^2$—$CHR^3$—$CR^4(CH_2)_o$—$(CR^5)_t$—$(CH_2)_v$—CE—$C_wH_{2w}$—$R^6$, where $Z^1 + Z^2 = Z$. The methods preferably used for this are those customary in peptide synthesis, as are described, for example, in Houben-Weyl, l. c., Volume 15/II, pages 1–806 (1974).

The reaction is preferably effected in the presence of a dehydrating agent, for example a carbodiimide such as DCCI or dimethylaminopropylethylcarbodiimide, or else propanephosphonic anhydride (compare Angew. Chem. 92, 129 (1980)), diphenylphosphoryl azide or 2-ethoxy-N-ethoxycarbonyl-1,2-dihydroquinoline, in an inert solvent, for example a halogenareal hydrocarbon such as dichloromethane, an ether such as THF or dioxane, an amide such as DMF or dimethylacetamide, or a nitrile such as acetonitrile, at temperatures between about −10° and 40°, preferably between 0° and 30°.

It is also possible, in place of II or III, to use suitable reactive derivatives of these substances in the reaction, for example those in which reactive groups have undergone intermediate blocking with protective groups. The acid derivatives II can be used, for example, in the form of their activated esters which are preferably formed in situ, for example by addition of HOBt or N-hydroxysuccinimide.

Urea derivatives of the formula I [$R^1 = R^8$—N—H—CO— or $R^{11}$—$C_mH_{2m}$—$(T)_s$—$(V)_y$—$C_nH_{2n}$—N—H—CO—] can be obtained, for example, by reacting an appropriate isocyanate (for example of the formula $R^8$—NCO; which can be prepared from an amine of the formula $R^8$—$NH_2$ and phosgene) with an amine of the formula H—Z—$NR^2$—$CHR^3$—$CR^4$—$(CH_2)_o$—$(CR^5)_t$—$(CH_2)_v$—CE—$C_wH_{2w}$—$R^6$ (IIa), preferably in an inert solvent such as THF at temperatures between about −10° and 40°, preferably between 10° and 30°.

The starting materials of the formulae II and III are mostly known. Those which are unknown can be prepared by known methods, for example the abovementioned methods of peptide synthesis and of elimination of protective groups.

To prepare a compound of the formula I (a thioketal) in which b is 0, it is furthermore possible to react a carbonyl compound of the formula IV with a dithiol of the formula V, preferably 1,3-propanedithiol, or with one of its salts, preferably the di-Na or di-K salt, preferably in one of the indicated inert solvents, for example a halogenated hydrocarbon such as dichloromethane, in the presence of a catalyst, for example of a Lewis acid such as $BF_3$ etherate, at temperatures between about $-10°$ and $60°$, preferably between $-5°$ and $10°$.

To prepare a disulfone of the formula I in which E is $-SO_2-CH_2-(CR^{17})_c-CH_2-SO_2$, it is possible to react a compound of the formula VI with a compound of the formula VII under alkylating conditions. X in the compounds of the formula VI is preferably Cl, Br or I; if X is an OH group esterified in a reactive way, it is preferably alkylsulfonyloxy with 1-6 C atoms, for example methanesulfonyloxy, or arylsulfonyloxy with 6-10 C atom, for example benzene-, p-toluene- or 1- or 2-naphthalenesulfonyloxy. In the reaction of VI with VII it is preferable first to prepare the reactive anion of VII by reaction with a strong base, for example NaH, in an inert solvent, for example an amide such as DMF; this is followed by addition of VI and allowing the reaction to go to completion at temperatures between about 0° and 60°.

Some of the starting materials of the formulae IV, V, VI and VII are known. Those which are unknown can be prepared by known methods in analogy to known substances.

It is furthermore possible to convert a compound of the formula I into another compound of the formula I, for example by functional modification of free amino and/or hydroxyl groups and/or oxidation of thioether groups to sulfoxide or sulfone groups and/or liberation of functionally modified amino and/or hydroxyl groups by solvolysis or hydrogenolysis and/or conversion of keto compounds into hydroxyl compounds by reduction or into amino compounds by reductive amination and/or alkylation of reactive CH groups.

Thus, for example, free hydroxyl and/or amino groups can be acylated in a customary manner, preferably in an inert solvent such as THF and/or in the presence of a base such as triethylamine or pyridine at temperatures between $-10°$ and $+30°$.

Compounds of the formula I in which $R^2$ is H and $R^3$ is OH can be converted by reaction with carbonyl compounds of the formula $R^8-CO-R^{13}$ or functional derivatives thereof (for example with ketals such as 2,2-dimethoxypropane) into cyclic aminals (oxazolidines) of the formula I in which $R^4$ is (H, $R^{12}$) and $R^2$ and $R^{12}$ together are $-CR^8R^{13}-O-$, preferably in the presence of an inert solvent such as toluene in the presence of a dehydration catalyst such as p-toluenesulfonic acid at temperatures between 30° and 120°.

Thioether groups, in particular in the radical E, can be oxidized to sulfoxide or sulfone groups, preferably with an oxidizing agent such as $H_2O_2$ or a peracid, for example 3-chloroperbenzoic acid or monoperoxyphthalic acid, or one of the salts thereof, in an inert solvent such as dichloromethane or THF at temperatures between about 0° and 40°. The sulfoxides are the main products with approximately stoichiometric amounts of $H_2O_2$, while the sulfones are mainly obtained with an excess of peracids.

If desired, it is possible for a functionally modified amino and/or hydroxyl group in a compound of the formula I to be liberated by solvolysis or hydrogenolysis by one of the methods described above.

Thus, for example, a compound of the formula I which contains an $R^{15}-C_xH_{2x}-O-CO-NH-$, an $AcNH-$, an $ArCH_2-SO_3-$ or an $AOOC-$ group can be converted into the corresponding compound of the formula I which contains in its stead an $H_2N-$, an $HSO_3-$ or an $HOOC-$ group, preferably by selective solvolysis by one of the methods indicated above.

$AOOC-$ groups can be hydrolyzed, for example, with NaOH or KOH in water/dioxane at temperatures between 0° and 40°, preferably 10° and 30°.

Furthermore, for example, keto compounds of the formula I ($R^4=O$) can be reduced to compounds of the formula I ($R^4=(H, OH)$), for example with a complex metal hydride such as $NaBH_4$ which does not simultaneously reduce the peptide carbonyl groups, in an inert solvent such as methanol at temperatures between about $-10°$ and $+30°$.

Keto compounds of the formula I ($R^4=O$) can also be converted into compounds of the formula I ($R^4=H, NH_2$) by reductive amination. The reductive amination can be carried out in one or more stages. Thus, for example, the keto compound can be treated with ammonium salts, for example ammonium acetate and $NaCNBH_3$, preferably in an inert solvent, for example an alcohol such as methanol, at temperatures between about 0° and 50°, in particular between 15° and 30°. It is furthermore possible initially to convert the keto compound into the oxime, using hydroxylamine in a customary manner, and to reduce the oxime to the amine, for example by catalytic hydrogenation on Raney nickel.

It is furthermore possible to alkylate reactive CH groups, for example to react compounds of the formula I in which w is 0, $R^6$ is H and b is 2 with compounds of the formula $R^6-C_wH_{2w}-X$ in which $R^6$ is different from H and/or w is different from 0, preferably under conditions similar to those indicated above for the reaction of VI with VII.

A base of the formula I can be converted into the relevant acid addition salt using an acid. Particularly suitable acids for this reaction are those which provide physiologically acceptable salts, thus it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and lauryl sulfuric acid. Salts with physiologically unacceptable acids, for example picrates, can be used to isolate and/or purify the compounds of the formula I.

The new compounds of the formula I and the physiologically acceptable salts thereof can be used to prepare pharmaceutical products by converting them, together with at least one vehicle or auxiliary and, if desired, together with one or more other active compound(s), into a suitable dosage form. The compositions obtained in this way can be used as medicaments in human or veterinary medicine. Suitable vehicles are organic or inorganic substances which are suitable for enteral (for example oral or rectal) or parenteral administration or for administration in the form of a spray for inhalation and which do not react with the new compounds, for example water, vegetable oils, benzyl alcohols, polyethylene glycols, glycerol triacetate and other fatty acid glycerides, gelatine, soya lecithin, carbohydrates such as lactose or starch, magnesium stearate, talc and cellulose. Used orally are, in particular, tablets, coated tablets, capsules, syrups, elixirs or drops; specifically of interest are lacquered tablets and capsules with enteric coatings or capsule shells. Used rectally are suppositories, and for parenteral administration are solutions, preferably oily or aqueous solutions as well as suspensions, emulsions or implants. For administration by spray for inhalation, it is possible to use sprays which contain the active substance either dissolved or suspended in a propellant gas mixture (for example chlorofluorohydrocarbons). The active substance is preferably used for this in micronized form, with one or more additional physiologically tolerated solvents possibly being present, for example ethanol. Solutions for inhalation can be administered with the aid of customary inhalers. The new compounds can also be freeze-dried and the resulting lyophilizates used, for example, to prepare products for injection. The stated compositions' can be sterilized and/or contain auxiliaries such as preservatives, stabilizers and/or wetting agents, emulsifiers, salts to influence the osmotic pressure, buffer substances, colorants and/or flavorings. They can, if desired, also contain one or more other active substances, for example one or more vitamins.

The substances according to the invention are, as a rule, administered in analogy to other known, commercially available peptides, but especially in analogy to the compounds described in EP-A 249,096, preferably in dosages about 10 mg–1 g, in particular 50–500 mg, per dosage unit. The daily dosage is preferably about 0.2–20 mg/kg, in particular 1–10 mg/kg, of body weight. The specific dose for each particular patient depends, however, on a wide variety of factors, for example on the activity of the specific compound used, on the age, body weight, general state of health and sex, on the diet, on the time and route of administration and on the rate of excretion, medicinal substance combination and severity of the particular disease for which the therapy is applied. Parenteral administration is preferred.

Renin-dependent hypertension and hyperaldosteronism as well as, furthermore, disorders caused by retroviruses, especially AIDS (acquired immunodeficiency syndrome), can be effectively treated by administration of dosages of, in particular, about 0.2–20, preferably 1–10, mg/kg of body weight. For diagnostic purposes, it is possible and preferable for the new compounds to be administered in single doses between about 0.1 and 10 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 40 04 898.5, filed Feb. 16, 1990 (published Aug. 22, 1991), are hereby incorporated by reference.

EXAMPLES

In the examples which follow, "usual working up" means: if necessary, water is added, the pH is adjusted to between 2 and 8, depending on the constitution of the final product, extraction is carried out with ethyl acetate or dichloromethane, the organic phase is separated off, dried over sodium sulfate, filtered and concentrated, and purification is carried out by chromatography on silica gel and/or crystallization. MS=mass spectrum; FAB=mass spectrum by the fast atom bombardment method.

Example 1

A mixture of 0.66 g of 2-[(2S,3S)-3-BOC-Phe-(imi-DNP-His)-amino-4-cyclohexyl-2-hydroxybutyl]-1,3-dithiane [FAB=840, diastereomer mixture; obtainable from 2-[(2S, 3S )-3-amino-4-cyclohexyl-2-hydroxybutyl]-1,3-dithiane (cf. Example 12) and BOC-Phe-(imi-DNP-His)-OH, by the method of Example 3], 15 ml of DMF, 3 ml of water and 0.3 ml of 5% NaHCO$_3$ solution is mixed with 0.22 g of 2-mercaptoethanol and left to stand at 20° for 17 h. The usual working up (silica gel, dichloromethane/methanol saturated with NH$_3$) provides 2 diastereomers of 2-[(2S, 3S )-3-BOC-Phe-His-amino-4-cyclohexyl-2-hydroxybutyl]-1,3-dithiane; m.p. 140°–145° (FAB 674) and m.p. 90°–92° (decomposition; FAB 674) respectively.

The following 1,3-dithiane 1,1,3,3-tetroxides are obtained analogously from the corresponding imi-DNP-His derivatives:

2-[(2S, 3S )-3-BOC-Phe-His-amino-4-cyclohexyl-2-hydroxybutyl]-, m.p. 231°–232° (decomp.); FAB 738; obtainable via 2-[(2S, 3S )-3-BOC-( imi-DNP-His )-amino-4-cyclohexyl-2-hydroxybutyl]-1,3-dithiane 1,1,3,3-tetroxide [m.p. 188°–190° (decomp.)] and 2-[(2S,3S)-3-H-(imi-DNP-His)-amino-4-cyclohexyl-2-hydroxybutyl ]-1,3-dithiane 1,1,3,3-tetroxide [m.p. 203° (decomp.)]

2-[(2S, 3S )-3-BOC-Phe-His-amino-4-cyclohexyl-2-hydroxybutyl]-2-methyl-, m.p. 145° (decomp.); FAB 752; obtainable via 2-[(2S,3S)-3-BOC-(imi-DNP-His)-amino-4-cyclohexyl-2-hydroxybutyl]-2-methyl-1,3-dithiane 1,1,3,3-tetroxide[mp. 125°–130° (decomp.); FAB 771 ]and 2-[(2-S,3S)-3-H-(imi-DNP-His)-amino-4-cyclohexyl-2-hydroxybutyl]-2-methyl-1,3-dithiane 1,1,3,3-tetroxide[m.p. 228° (decomp.)]

2-[(2S, 3S )-3-(4-BOC-amino-piperidinocarbonyl-Phe-His-amino)-4-cyclohexyl-2-hydroxybutyl ]-, FAB 865

2-[(2S, 3S)-3-(4-BOC-amino-piperidinocarbonyl-Phe-His-amino)-4-cyclohexyl-2-hydroxybutyl ]-2-methyl-, FAB 879

2-[(2S, 3S)-3-(3-BOC-amino-3-methyl-butyryl-Mal-His-amino)-4-cyclohexyl-2-hydroxybutyl ]-, FAB 867

2-[(2S, 3S)-3-(3-BOC-amino-3-methyl-butyryl-Mal-His-amino)-4-cyclohexyl-2-hydroxybutyl ]-2-methyl-, FAB 881

2-[(2S, 3S)-3-(2-benzyl-3-tert.-butylsulfonyl-propionyl-His-amino)-4-cyclohexyl-2-hydroxybutyl-3-, 2 isomers, FAB of each 757 ;one of them yields a hydrochloride,m.p. 175°–180° (decomp.)

2-[(2S, 3S)-3-(2-benzyl-3-tert.-butylsulfonyl-propionyl-His-amino)-4-cyclohexyl-2-hydroxybutyl ]-2-methyl-, 2 isomers, FAB of each 771

2-[(2S, 3S)-3-BOC-Mal-His-amino-4-cyclohexyl-2-hydroxybutyl]

2-[(2S, 3S)-3-morpholinocarbonyl-Phe-His-amino-4-cyclohexyl-2- hydroxybutyl]

2-[(2S, 3S)-3-BOC-Pro-Phe-His-amino-4-cyclohexyl-2-hydroxybutyl]

2-[(3S, 4S)-4-BOC-Phe-His-amino-5-cyclohexyl-3-hydroxypentyl]-, m.p. 170°–174° (decomp.), FAB 753; obtainable via 2-[(3S, 4S)-4-BOC-(imi-DNP-His)-amino-5-cyclohexyl-3-hydroxy-pentyl]-1,3-dithiane 1,1,3,3-tetroxide (m.p. 132°–135°; FAB 771) and 2-[(3S,4S)-4-H-(imi-DNP-His)-amino-5-cyclohexyl-3-hydroxy-pentyl ]-1,3-dithiane 1,1,3,3-tetroxide [m.p. 205°–210° (decomp.); FAB 671]

2-[(3S, 4S)-4-BOC-Phe-His-amino-5-cyclohexyl-3-hydroxypentyl]-2-methyl-, m.p. 118°–122 ° (decomp.), FAB 766; obtainable via 2-[(3S,4S)-4-BOC-(imi-DNP-His)-amino-5-cyclohexyl-3-hydroxy-pentyl]-2-methyl-1,3-dithiane 1,1,3,3-tetroxide, [m.p. 136°–140° (decomp.); FAB 785] and 2-[(3S, 4S)-4-H-(imi-DNP-His )-amino-5-cyclohexyl-3-hydroxy-pentyl]-2 -methyl-1,3-dithiane 1,1,3,3-tetroxide [m.p. 211°–214° (decomp.); FAB 685]

2-[(3S, 4S)-4-(4-BOC-amino-piperidinocarbonyl )-Phe-His-amino-5-cyclohexyl-3-hydroxy-pentyl]-, FAB 878

2-[(3S, 4S)-4-(4-BOC-amino-piperidinocarbonyl )-Phe-His-amino-5-cyclohexyl-3-hydroxy-pentyl]-2-methyl-, m.p. 158°–162 ° (decomp.), FAB 892

2-[(3S, 4S)-4-(3-BOC-amino-3-methyl-butyryl-Mal-His-amino)-5-cyclohexyl-3-hydroxy-pentyl]-, m.p. 130°–135 ° (decomp.), FAB 881

2-[(3S ,4S)-4-(3-BOC-amino-3-methyl-butyryl-Mal-His-amino)-5-cyclohexyl-3-hydroxy-pentyl ]-2-methyl-, m.p. 122°–126 ° (decomp.); FAB 895

2-[(3S, 4S)-4-(2-benzyl-3-tert.-butylsulfonyl-propionyl-His-amino)-5-cyclohexyl-3-hydroxy-pentyl]- , m.p. 230° (decomp.) ;FAB771

2-[(3S, 4S)-4-(2-benzyl-3-tert.-butylsulfonyl-propionyl-His-amino)-5-cyclohexyl-3-hydroxy-pentyl]-2 -methyl-; m.p. 230° (decomp.); FAB 771.

Example 2

1 g of 2-[(2S,3S)-3-BOC-Phe-(imi-BOM-His)-amino-4-cyclohexyl-2-hydroxybutyl ]-1,3-dithiane 1,1,3,3-tetroxide [obtainable from 2-[(2S,3S)-3-amino-4-cyclohexyl-2-hydroxybutyl ]-1,3-dithiane 1,1,3,3-tetroxide (cf. Example 12) and BOC-Phe-(imi-BOM-His)-OH by the method of Example 3] is dissolved in 25 ml of ethanol and hydrogenated on 0.4 g of 10% Pd-C at 20° and 1 bar until $H_2$ uptake is complete, and the mixture is filtered and evaporated to give, after purification by chromatography, 2-[(2S, 3S)-3-BOC-Phe-His-amino-4-cyclohexyl-2-hydroxybutyl]-1,3-dithiane 1,1,3,3-tetroxide; m.p. 231°–232° FAB 738.

Example 3

A solution of 3.21 g of 2-[(2S,3S)-3-amino-4-cyclohexyl-2-hydroxybutyl ]-1,3-dithiane 1,1,3,3-tetroxide in 60 ml of dichloromethane is mixed with 1.01 g of N-methylmorpholine. To the stirred mixture are added 2.31 g of BOC-Leu-OH, 1.35 g of HOBt and a solution of 2.06 g of DCCI in 50 ml of dichloromethane, the mixture is stirred at 2°–6° for 14 h, the precipitated dicyclohexylurea is filtered off, and the filtrate is evaporated. The usual working up results in 2-[(2S,3S)-3-BOC-Leu-amino-4-cyclohexyl-2-hydroxybutyl]-1,3-dithiane 1,1,3,3-tetroxide, m.p. 228° ; FAB 567.

The following 1,3-dithiane 1,1,3,3-tetroxides are obtained analogously:

2-[(2S,3S)-3-BOC-Phe-amino-4-cyclohexyl-2-hydroxybutyl]

2-[(2S,3S)-3-BOC-Phe-βAla-amino-4-cyclohexyl-2-hydroxybutyl]

2-[(2S,3S)-3-BOC-Phe-Gly-amino-4-cyclohexyl-2-hydroxybutyl]

2-[(2S,3S)-3-BOC-Phe-Ile-amino-4-cyclohexyl-2-hydroxybutyl]

2-[(2S,3S)-3-BOC-Phe-Leu-amino-4-cyclohexyl-2-hydroxybutyl]

2-[(2S,3S)-3-BOC-Phe-Nle-amino-4-cyclohexyl-2-hydroxybutyl]

2-[(2S,3S)-3-BOC-Phe-Nva-amino-4-cyclohexyl-2-hydroxybutyl]

2-[(2S,3S)-3-BOC-Phe-Val-amino-4-cyclohexyl-2-hydroxybutyl]

2-[(2S,3S)-3-BOC-Mal-amino-4-cyclohexyl-2-hydroxybutyl]

2-[(2S,3S)-3-BOC-Mal-βAla-amino-4-cyclohexyl-2-hydroxybutyl]

2-[(2S,3S)-3-BOC-Mal-Gly-amino-4-cyclohexyl-2-hydroxybutyl]

2-[(2S,3S)-3-BOC-Mal-Ile-amino-4-cyclohexyl-2-hydroxybutyl]

2-[(2S,3S)-3-BOC-Mal-Leu-amino-4-cyclohexyl-2-hydroxybutyl]

2-[(2S,3S)-3-BOC-Mal-Nle-amino-4-cyclohexyl-2-hydroxybutyl]

2-[(2S,3S)-3-BOC-Mal-Nva-amino-4-cyclohexyl-2-hydroxybutyl]

2-[(2S,3S)-3-BOC-Mal-Val-amino-4-cyclohexyl-2-hydroxybutyl]

2-[(2S,3S)-3-BOC-Pro-Phe-amino-4-cyclohexyl-2-hydroxybutyl]

2-[(2S, 3S)-3-BOC-Pro-Phe-βAla-amino-4-cyclohexyl-2-hydroxybutyl]

2-[(2S, 3S)-3-BOC-Pro-Phe-Gly-amino-4-cyclohexyl-2-hydroxybutyl]

2-[(2S, 3S)-3-BOC-Pro-Phe-Ile-amino-4-cyclohexyl-2hydroxybutyl]

2-[(2S, 3S)-3-BOC-Pro-Phe-Leu-amino-4-cyclohexyl-2hydroxybutyl]

2-[(2S, 3S)-3-BOC-Pro-Phe-Nle-amino-4-cyclohexyl-2hydroxybutyl]

2-[(2S, 3S)-3-BOC-Pro-Phe-Nva-amino-4-cyclohexyl-2hydroxybutyl]

2-[(2S, 3S)-3-BOC-Pro-Phe-Val-amino-4-cyclohexyl-2hydroxybutyl]

2-[(2S, 3S)-3-(4-BOC-amino-piperidinocarbonyl-Phe-amino)-4-cyclohexyl-2-hydroxybutyl]-, m.p. 185°–190° , FAB 727

2-[(2S, 3S)-3-(4-BOC-amino-piperidinocarbonyl-Phe-βAla-amino)-4-cyclohexyl-2-hydroxybutyl ]- ,m.p. 133°–135°, FAB 798

2-[(2S, 3S)-3-(4-BOC-amino-piperidinocarbonyl-Phe-Gly-amino)-4-cyclohexyl-2-hydroxybutyl]

2-[(2S, 3S)-3-(4-BOC-amino-piperidinocarbonyl-Phe-Ile-amino)-4-cyclohexyl-2-hydroxybutyl]

2-[(2S, 3S)-3-(4-BOC-amino-piperidinocarbonyl-Phe-Leu-amino)-4-cyclohexyl-2-hydroxybutyl ]-, FAB 840

2-[(2S, 3S)-3-(4-BOC-amino-piperidinocarbonyl-Phe-Nle-amino)-4-cyclohexyl-2-hydroxybutyl ]- , m.p. 156–°163°, FAB 840

2-[(2S, 3S)-3-(4-BOC-amino-piperidinocarbonyl-Phe-Nva-amino)-4-cyclohexyl-2-hydroxybutyl ]- m.p. 154°–157°, FAB 826

2-[(2S, 3S)-3-(4-BOC-amino-piperidinocarbonyl-Phe-Val-amino)-4-cyclohexyl-2-hydroxybutyl ]- ,m.p. 185°–188°, FAB 826

2-[(2S, 3S)-3-(morpholinocarbonyl-Phe-amino )-4-cyclohexyl-2-hydroxybutyl]

2-[(2S, 3S)-3-(morpholinocarbonyl-Phe-βAla-amino )-4-cyclohexyl-2-hydroxybutyl ]

2-[(2S, 3S)-3-(morpholinocarbonyl-Phe-Gly-amino )-4-cyclohexyl-2-hydroxybutyl]

2-[(2S, 3S)-3-(morpholinocarbonyl-Phe-Ile-amino )-4-cyclohexyl-2-hydroxybutyl]

2-[(2S, 3S)-3-(morpholinocarbonyl-Phe-Leu-amino)-4-cyclohexyl-2-hydroxybutyl]

2-[(2S, 3S)-3-(morpholinocarbonyl-Phe-Nle-amino)-4-cyclohexyl-2 -hydroxybutyl]

2-[(2S, 3S)-3-(morpholinocarbonyl-Phe-Nva-amino )-4-cyclohexyl-2-hydroxybutyl]

2-[(2S, 3S)-3-(morpholinocarbonyl-Phe-Val-amino )-4-cyclohexyl-2-hydroxybutyl]

Example 4

2-[(2S,3S)-3-(3-BOC-amino-3-methyl-butyryl-Phe-αAla-amino)-butyl]-1,3-dithiane 1,1,3,3-tetroxide is obtained in analogy to Example 3 from 3-BOC-amino-3-methylbutyric acid and 2-[(2S,3S)-4-cyclohexyl-2-hydroxy-3-(H-Phe-βAla-amino)-butyl]-1,3-dithiane 1,1,3,3-tetroxide.

Example 5

2-[(2S,3S)-3-(4-BOC-amino-piperidinocarbonyl-Phe-Leu-amino)-4-cyclohexyl-2-hydroxybutyl]-1,3-dithiane 1,1,3,3-tetroxide, FAB 840, is obtained in analogy to Example 3 from N-(4-BOC-amino-piperidinocarbonyl)-Phe-OH and 2-[(2S,3S)-4-cyclohexyl-2-hydroxy-3-(H-Leu-amino)butyl]-1,3-dithiane 1,1,3,3-tetroxide (Example 11).

Example 6

A mixture of 1.02 g of 3-BOC-4-cyclohexylmethyl-2,2-dimethyl-5-oxazolidinyl-acetaldehyde and 30 ml of $CH_2Cl_2$ is mixed at 0° with 0.37 g of 1,3-propanedithiol and 0.13 ml of $BF_3$ etherate. The mixture is washed with $NaHCO_3$ solution and then evaporated and chromatographed (silica gel, $CH_2Cl_2$/ether 95:5) to give 2-[(2S,3S)-3-BOC-amino-4-cyclohexyl-2-hydroxybutyl]-1,3-dithiane, colorless resin, MS: 389.

Example 7

A stirred solution of 0.9 g of 1,3-dithiane 1,1,3,3-tetroxide in 10 ml of DMF is mixed at 20° with 0.15 g of 80% NaH. After 30 min, 2.1 g of 2-[(4S,5S)-3-BOC-4-cyclohexylmethyl-2,2-dimethyl-5-oxazolidinyl]ethyl methanesulfonate are added. The mixture is stirred at 50° for 19 h and diluted with water, and the resulting 2-[2-((4S,5S)-3-BOC-4-cyclohexylmethyl-2,2-dimethyl-5-oxazolidinyl)-ethyl]-1,3-dithiane 1,1,3,3-tetroxide is filtered off, washed with ether and dried, m.p. 199°-200°; MS 507.

2-[2-((4S,5S)-3-BOC-4-cyclohexylmethyl-2,2-dimethyl-5-oxazolidinyl)-ethyl]-2-ethoxycarbonyl-1,3-dithiane 1,1,3,3-tetroxide, FAB 581, is obtained analogously using 2-ethoxycarbonyl-1,3-dithiane 1,1,3,3-tetroxide.

Example 8

A mixture of 4.68 g of 2-[(2S,3S)-3-BOC-amino-4-cyclohexyl-2-hydroxybutyl]-1,3-dithiane, 5.83 g of 2,2-dimethoxypropane, 100 ml of toluene and 97 mg of p-toluenesulfonic acid is boiled for 2 h, cooled, washed with 2 N give NaOH and then with water and evaporated to give 2-[(4S,5S)-3-BOC-4-cyclohexylmethyl-2,2-dimethyl-5-oxazolidinyl-methyl]-1,3-dithiane, m.p. 104°-106°.

Example 9

A mixture of 3.89 g of 2-[(2S,3S)-3-BOC-amino-4-cyclohexyl-2-hydroxybutyl]-l,3-dithiane, 200 ml of dichloromethane and 15.7 g of 55% 3-chloroperbenzoic acid is stirred at 20° for 3 h. The mixture is filtered, the filtrate is washed with 2N NaOH and then with saturated NaCl solution, and the usual working up is continued to give 2-[(2S,3S)-3-BOC-amino-4-cyclohexyl-2-hydroxybutyl]-1,3-dithiane 1,1,3,3-tetroxide, m.p. 186°-188°.

Example 10

A mixture of 14.21 g of 2-[(4S,5S)-3-BOC-4-cyclohexylmethyl-2,2-dimethyl-5-oxazolidinyl-methyl ]-1,3-dithiane, 65 g of Mg monoperoxyphthalate hexahydrate and 300 ml of THF is stirred at 20° for 16 h. Working up is carried out with ether/dilute sodium hydroxide solution to give 2-[(4S, 5S)-3-BOC-4-cyclohexylmethyl-2,2-dimethyl-5-oxazolidinylmethyl]-1,3-dithiane 1,1,3,3-tetroxide, m.p. 219°-220°.

Example 11

A mixture of 4.17 g of 2-[(4S,5S)-3-BOC-4-cyclohexylmethyl-2,2-dimethyl-5-oxazolidinyl-methyl]-1,3-dithiane, 2.5 ml of 30% $H_2O_2$ and 40 ml of acetic acid is stirred at 20° for 16 h. The usual working up results in 2-[(4S,5S)-3-BOC-4-cyclohexylmethyl-2,2-dimethyl-5-oxazolidinyl-methyl]-1,3-dithiane 1,3-dioxide.

Example 12

A solution of 1 g of 2-[(2S,3S)-3-BOC-amino-4-cyclohexyl-2-hydroxybutyl]-l,3-dithiane in 30 ml of ethyl acetate saturated with HCl gas is stirred at 0° for 16 h. The precipitated 2-[(2S,3S)-3-amino-4-cyclohexyl-2-hydroxybutyl]-1,3-dithiane hydrochloride is filtered off and washed with ethyl acetate and then with ether. M.p. 144°-147° (decomp.).

The following are obtained analogously from the corresponding BOC compounds:

2-[(2S,3S)-3-amino-4-cyclohexyl-2-hydroxybutyl]-2-methyl-1,3-dithiane

2-[(3S,4S)-4-amino-5-cyclohexyl-3-hydroxypentyl]-1,3-dithiane

2-[(3S,4S)-4-amino-5-cyclohexyl-3-hydroxypentyl]-2-methyl-1,3-dithiane as are the following 1,3-dithiane 1,1,3,3-tetroxides:

2-[(2S,3S)-3-amino-4-cyclohexyl-2-hydroxybutyl]-hydrochloride, m.p. 240°-242° (decomp.)

2-[(2S,3S)-3-amino-4-cyclohexyl-2-hydroxybutyl]-2-methyl

2-[(2S, 3S)-4-cyclohexyl-2-hydroxy-3-(H-Leu-amino )butyl]-, foam

2-[(2S, 3S)-4-cyclohexyl-2-hydroxy-3-(H-Leu-amino)-butyl]-2-methyl

2-[(2S, 3S),4-cyclohexyl-2-hydroxy-3-H-Phe-His-amino-butyl]-, FAB 638

2 -[(2S, 3S)-4-cyclohexyl-2-hydroxy-3-H-Phe-His-aminobutyl]-2-methyl

2-[(2S, 3S)-3-(4-aminopiperidinocarbonyl-Phe-His-amino)-4-cyclohexyl-2-hydroxybutyl]-, m.p. 163° (decomp.), FAB 764; dihydrochoride, m.p. 191°-195°, FAB 764

2-[(2S, 3S)-3-(4-aminopiperidinocarbonyl-Phe-His-amino)-4-cyclohexyl-2-hydroxybutyl ]-2-methyl-, m.p. 155 ° (decomp.), FAB 778

2-[(2S, 3S)-3-(4-aminopiperidinocarbonyl-Phe-Leu-amino)-4-cyclohexyl-2-hydroxybutyl]-, m.p. 157° (decomp.), FAB 740; hydrochloride, m.p. 181°–184° (decomp.), FAB 740

2-[(2S, 3S)-3-(4-aminopiperidinocarbonyl-Phe-Leu-amino)-4-cyclohexyl-2-hydroxybutyl]-2-methyl 2-[(2S, 3S)-3-(3-amino-3-methyl-butyryl)-Mal-His-amino)-4-cyclohexyl-2-hydroxybutyl]-, FAB 767

2-[(2S, 3S)-3-(3-amino-3-methyl-butyryl)-Mal-His-amino)-4-cyclohexyl-2-hydroxybutyl]-2-methyl-, FAB 781

2-[(2S, 3S)-3-Mal-His-amino-4-cyclohexyl-2-hydroxybutyl]

2-[(2S, 3S)-3-Pro-Phe-His-amino-4-cyclohexyl-2-hydroxybutyl]

2-[(2S, 3S)-3-H-Phe-amino-4-cyclohexyl-2-hydroxybutyl]

2-[(2S, 3S)-3-H-Phe-βAla-amino-4-cyclohexyl-2-hydroxybutyl]

2-[(2S, 3S)-3-H-Phe-Gly-amino-4-cyclohexyl-2-hydroxybutyl]

2-[(2S, 3S)-3-H-Phe-Ile-amino-4-cyclohexyl-2-hydroxybutyl]

2-[(2S, 3S)-3-H-Phe-Leu-amino-4-cyclohexyl-2-hydroxybutyl]

2-[(2S, 3S)-3-H-Phe-Nle-amino-4-cyclohexyl-2-hydroxybutyl]

2-[(2S, 3S)-3-H-Phe-Nva-amino-4-cyclohexyl-2-hydroxybutyl]

2-[(2S, 3S)-3-H-Phe-Val-amino-4-cyclohexyl-2-hydroxybutyl]

2-[(2S,3S)-3-H-Mal-amino-4-cyclohexyl-2-hydroxybutyl]

2-[(2S,3S)-3-H-Mal-βAla-amino-4-cyclohexyl-2-hydroxybutyl]

2-[(2S,3S)-3-H-Mal-Gly-amino-4-cyclohexyl-2-hydroxybutyl]

2-[(2S,3S)-3-H-Mal-Ile-amino-4-cyclohexyl-2-hydroxybutyl]

2-[(2S,3S)-3-H-Mal-Leu-amino-4-cyclohexyl-2-hydroxybutyl]

2-[(2S,3S)-3-H-Mal-Nle-amino-4-cyclohexyl-2-hydroxybutyl]

2-[(2S,3S)-3-H-Mal-Nva-amino-4-cyclohexyl-2-hydroxybutyl]

2-[(2S,3S)-3-H-Mal-Val-amino-4-cyclohexyl-2-hydroxybutyl]

2-[(2S, 3S)-3-H-Pro-Phe-amino-4-cyclohexyl-2-hydroxybutyl]

2-[(2S, 3S)-3-H-Pro-Phe-βAla-amino-4-cyclohexyl-2-hydroxybutyl]

2-[(2S, 3S)-3-H-Pro-Phe-Gly-amino-4-cyclohexyl-2-hydroxybutyl]

2-[(2S, 3S)-3-H-Pro-Phe-Ile-amino-4-cyclohexyl-2-hydroxybutyl]

2-[(2S, 3S)-3-H-Pro-Phe-Leu-amino-4-cyclohexyl-2-hydroxybutyl]

2-[(2S, 3S)-3-H-Pro-Phe-Nle-amino-4-cyclohexyl-2-hydroxybutyl]

2-[(2S, 3S)-3-H-Pro-Phe-Nva-amino-4-cyclohexyl-2-hydroxybutyl]

2-[(2S, 3S)-3-H-Pro-Phe-Val-amino-4-cyclohexyl-2-hydroxybutyl]

2-[(2S, 3S)-3-(4-amino-piperidinocarbonyl-Phe-amino)-4-cyclohexyl-2-hydroxybutyl]

2-[(2S, 3S)-3-(4-amino-piperidinocarbonyl-Phe-βAla-amino)-4-cyclohexyl-2-hydroxybutyl]

2-[(2S, 3S)-3-(4-amino-piperidinocarbonyl-Phe-Gly-amino)-4-cyclohexyl-2-hydroxybutyl]

2-[(2S,3S)-3-(4-amino-piperidinocarbonyl-Phe-Ile-amino)-4-cyclohexyl-2-hydroxybutyl]

2-[(2S,3S)-3-(4-amino-piperidinocarbonyl-Phe-Ile-amino)-4-cyclohexyl-2-hydroxybutyl]-, m.p. 140°–45°, FAB 741; hydrochloride, m.p. 184°–189°, FAB 740

2-[(2S,3S)-3-(4-amino-piperidinocarbonyl-Phe-Nva-amino)-4-cyclohexyl-2-hydroxybutyl]-, m,p. 148°–153°, FAB 727; hydrochloride, m,p. 207°–212°, FAB 716

2-[(2S,3S)-3-(4-amino-piperidinocarbonyl-Phe-Val-amino)-4-cyclohexyl-2-hydroxybutyl]-, m,p, 190°–192°, FAB 726; hydrochloride, m.p. 200°–205°, FAB 726.

2-[(3S, 4S)-4-amino-5-cyclohexyl-3-hydroxypentyl]

2-[(3S,4S)-4-amino-5-cyclohexyl-3-hydroxypentyl]-2-methyl

2-[(3S,4S)-5-cyclohexyl-3-hydroxy-4-H-Phe-His-aminopentyl]

2-[(3S,4S)-5-cyclohexyl-3-hydroxy-4-H-Phe-His-aminopentyl]-2-methyl

2-[(3S, 4S)-4-(4-aminopiperidinocarbonyl-Phe-His-amino)-5-cyclohexyl-3-hydroxypentyl]-, m.p. 156°–158° (decomp.), FAB 779

2-[(3S, 4S)-4-(4-aminopiperidinocarbonyl,Phe-His-amino)-5-cyclohexyl-3-hydroxypentyl]-2-methyl-, m.p 185°–190° FAB 792

2-[(3S,4S)-4-(4-aminopiperidinocarbonyl-Phe-Leu-amino)-5-cyclohexyl-3-hydroxypentyl]

2-[(3S,4S)-4-(4-aminopiperidinocarbonyl-Phe-Leu-amino)-5-cyclohexyl-3-hydroxypentyl]-2-methyl 2-[(3S,4S)-4-(3-amino-3-methyl-butyryl-Mal-His-amino)-5-cyclohexyl-3-hydroxypentyl]-, m.p. 188°–192°, FAB 781

2-[(3S,4S)-4-(3-amino-3-methyl-butyryl-Mal-His-amino)-5-cyclohexyl-3-hydroxypentyl]-2-methyl

Example 13

A solution of 0.98 g of 2-[(4S,5S)-3-BOC-4-cyclohexylmethyl-2,2-dimethyl-5-oxazolidinyl-methyl]-1,3-dithiane 1,1,3,3-tetroxide in 300 ml of THF is mixed at −30° with 1.3 ml of a 1.6 molar solution of butyl-Li in hexane. The mixture is stirred for 1 h and then 0.56 g of methyl iodide is added and the mixture is stirred for 24 h in a thawing cooled bath, diluted with 50 ml of ether, and worked up as usual to give 2-[(4S,5S)-3-BOC-4-cyclohexylmethyl-2,2-dimethyl-5-oxazolidinyl-methyl]-2-methyl-1,3-dithiane 1,1,3,3-tetroxide, m.p. 176°–177°.

Example 14

A solution of 1.02 g of 2-[2-(4S,5S)-3-BOC-4-cyclohexylmethyl-2,2-dimethyl-5-oxazolidinyl)-ethyl]-1,3-dithiane 1,1,3,3-tetroxide in 30 ml of THF is mixed at −30° with 2.6 ml of a 1.6M $C_4H_9Li$ solution in hexane. The mixture is stirred at −30° for 2 h, 0.35 ml of $CH_3I$ is added, and the mixture is stirred at −35° for 1.5 h and then at 20° for 24 h, and worked up as usual to give 2-[2-((4S,5S)-3-BOC-4-cyclohexylmethyl-2,2-dimethyl-5-oxazolidinyl)-ethyl]-2-methyl-1,3-dithiane 1,1,3,3-tetroxide, m.p. 193°–196°.

Example 15

The product obtained as in Example 13 is treated with HCl/ethyl acetate and worked up in analogy to Example 12. Simultaneous elimination of the BOC and the acetonide groups results in 2-[(2S,3S)-3-amino-4- cyclohexyl-2-hydroxybutyl]-2-methyl-1,3-dithiane 1,1,3,3-tetroxide, m.p. 171°–174°.

The following are obtained analogously from the corresponding N-BOC-oxazolidines:

2-[(2S,3S)-3-amino-4-cyclohexyl-2-hydroxybutyl]-1,3-dithiane 1,1,3,3-tetroxide

2-[(3S,4S)-4-amino-5-cyclohexyl-3-hydroxypentyl]-1,3-dithiane 1,1,3,3-tetroxide

2-[(3S,4S)-4-amino-5-cyclohexyl-3-hydroxypentyl]-2-methyl-1,3-dithiane 1,1,3,3-tetroxide

Example 16

A mixture of 1.19 g of phenyl isocyanate, 3.67 g of 2-[(2S,3S)-3-amino-4-cyclohexyl-2-hydroxybutyl ]-2-methyl- 1,3-dithiane 1,1,3,3-tetroxide, 1.01 g of triethylamine and 60 ml of dichloromethane is stirred at 20° for 5 h. The usual working up gives 2-[(2S,3S)-4-cyclohexyl-2-hydroxy-3-(N'-phenylureido)-butyl]-2-methyl-1,3-dithiane 1,1,3,3-tetroxide, m.p 238°–240°, FAB 487.

The following 1,3-dithiane 1,1,3,3-tetroxides are obtained analogously from the corresponding amino compounds:

2-[(2S,3S)-4-cyclohexyl-2-hydroxy-3-(N'-phenylureido)butyl]

2-[(3S,4S)-5-cyclohexyl-3-hydroxy-4-(N'-phenylureido)pentyl]

2-[(3S,4S)-5-cyclohexyl-3-hydroxy-4-(N'-phenylureido)pentyl]-2-methyl

2-[(4S,5S)-4-cyclohexyl-2,2-dimethyl-3-N-phenylcarbamoyl-5-oxazolidinyl]

2-[(4S,5S)-4-cyclohexyl-2,2-dimethyl-3-N-phenylcarbamoyl-5-oxazolidinyl]-2-methyl-, FAB 527

2-[2-((4S,5S)-4-cyclohexylmethyl-2,2-dimethyl-3-N-phenylcarbamoyl-5-oxazolidinyl)-ethyl]

2-[2-((4S,5S)-4-cyclohexylmethyl-2,2-dimethyl-3-N-phenylcarbamoyl-5-oxazolidinyl)-ethyl]-2-methyl-.

Example 17

A mixture of 1 g of 2-[2-((4S,5S)-3-BOC-4-cyclohexylethyl-2,2-dimethyl-5-oxazolidinyl)-ethyl]-2-ethoxycarbonyl-1,3-dithiane 1,1,3,3-tetroxide, 50 ml of dioxane and 20 ml of 2 N NaOH (aqueous) is stirred at 20° for 3 h. The usual working up gives 2-[2-((4S,5S)-3-BOC-4-cyclohexylmethyl-2,2-dimethyl-5-oxazolidinyl)-ethyl]-2-carboxy-1,3-dithiane 1,1,3,3-tetroxide.

Example 18

2-[(2S, 3S)-3-amino-4-cyclohexyl-2-hydroxybutyl]-1,3-dithiane 1,1,3,3 -tetroxide, hydrochloride, m.p. 240°–242° (decomp.), is obtained in analogy to Example 2 from 2-[(2S, 3S)-CBZ-amino-4-cyclohexyl-2-hydroxybutyl]-1,3-dithiane 1,1,3,3 -tetroxide by hydrogenolysis.

Example 19

In analogy to Example 1, the following 1,3-dithiane 1,1,3,3-tetroxides are obtained from the corresponding imi-DNP-His derivatives:

2-[(2S, 3S)-3-(4-BOC-amino-piperidinocarbonyl-Pla-His-amino)-4-cyclohexyl-2-hydroxy-butyl]-, FAB 865

2-[(4S, 5S)-5-(BOC-Phe-His-amino)-6-cyclohexyl-4-hydroxyhexyl]-, m.p. 150° (decomposition), FAB 766.

Example 20

In analogy to Example 3, there are obtained from 2-[(2S,3S)-3-amino-4-cyclohexyl-2-hydroxy-butyl]-1,3-dithiane 1, 1,3,3-tetroxide or from 2-[(3S, 4S)-4-amino-5-cyclohexyl-3-hydroxypentyl]-1,3-dithiane 1,1,3,3-tetroxide or from 2-[(4S,5S)-5-amino-6-cyclohexyl-4-hydroxy-hexyl ]-1,3-dithiane 1,1,3,3-tetroxide [dihydrochloride, m.p. 209°–210° , FAB 382, obtainable from (4S,5S)-3-BOC-4-cyclohexyl-methyl-5-(2-methansulfonyloxy-ethyl)-2,2-di-methyl-oxazolidine via the corresponding 5-(2-cyanoethyl)-, 5-(2-carboxyethyl)-(m.p. 190° (decomposition)), 5-(2-methoxy-carbonyl-ethyl)-(oil; FAB 384), 5-(3-hydroxy-propyl)-(m.p. 60°–61°; FAB 356) and 5-(3-methanesulfonyloxy-propyl)-compounds (m.p. 63°–64°, FAB 434), react ion of the last mentioned compound with 1,3-dithiane 1,1,3,3-tetroxide to yield 2-[3-((4S,5S)-3-BOC-4-cyclohexylmethyl-2,2-dimethyl-5-oxazolidinyl)-propyl]-1,3-dithiane 1,1,3,3-tetroxide (FAB 522) and cleavage with methanolic hydrochloric acid at 25° the following 1,3-dithiane 1,1,3,3-tetroxides:

2-[(3S, 4S)-4-(4-BOC-amino piperidinocarbonyl-Phe-βAla-amino)-5-cyclohexyl-3-hydroxy-pentyl]-, m.p. 143° (decomposition), FAB 812

2-[(3S, 4S)-4-BOC-Leu-Met (02 )-amino-5-cyclohexyl-3-hydroxypentyl]-, m.p. 212°–215°, FAB 744

2-[(3S, 4S)-4-(4-BOC-amino-piperidinocarbonyl-Phe-amino)-5-cyclohexyl-3-hydroxy-pentyl ]-, m.p. 192° (decomposition), FAB 741

2-[(2S, 3S)-3-anilino-carbonylamino-4-cyclohexyl-2-hydroxybutyl]-, m.p. 240°–241 °, FAB 473

2-[(3S, 4S)-4-(4-BOC-amino-piperidinocarbonyl-amino)-5-cyclohexyl-3-hydroxy-pentyl]-, m.p. 136° (decomposition), FAB 579 (with 4-BOC-amino-piperidino-carbonyl chloride)

2-[(2S, 3S)-3-BOC-Nva-amino-4-cyclohexyl-2-hydroxy-butyl]-, m.p. 228°–230°, FAB 553

2-[-(2S, 3S)-3-BOC-Nle-amino-4-cyclohexyl-2-hydroxy-butyl]-, m.p. 225°–226° , FAB 567

2-[(2S, 3S)-3-BOC-Val-amino-4-cyclohexyl-2-hydroxy-butyl]-, m.p. 235°–236°, FAB 553

2-[(2S, 3S)-3-(1 -BOC-amino-4-piperidyl-carbonyl-amino )-4-cyclohexyl-2-hydroxy-butyl]-, m.p. 215°–217°, FAB 565

2-[(3S, 4S)-4-(4-BOC-amino-piperidinocarbonyl-amino-Phe-Gln-amino)-5-cyclohexyl-3-hydroxy-pentyl]-, m.p. 170° (decomposition), FAB 869

2-[(2S, 3S)-3-(BOC-Met-amino)-4-cyclohexyl-2-hydroxy-butyl]-, m.p. 233°–234°, FAB 585

2-[(2S, 3S)-3-(BOC-Met(O₂)-amino)-4-cyclohexyl-2-hydroxybutyl]-, m.p. 227°–228°, FAB 617

2-[(2S,3S)-3-(4-BOC-amino-piperidinocarbonyl-Phe-Met-amino)-4-cyclohexyl-2-hydroxy-butyl]-, m.p. 167°–169°, FAB 858

2-[(2S, 3S)-3-(BOC-(S-Me-Cys)-amino)-4-cyclohexyl-2-hydroxybutyl]-, m.p. 222°–224°, FAB 571

2-[(3S, 4S)-4-(4-BOC-amino-piperidinocarbonyl-Phe-Asn-amino)-5-cyclohexyl-3-hydroxy-pentyl]-, m.p. 172° (decomposition), FAB 855

2-[(2S, 3S)-3-(4-BOC-amino-piperidinocarbonyl-Phe-(S-Me-Cys)-amino)-4-cyclohexyl-2-hydroxy-butyl]-, m.p. 161°–165°, FAB 844

2-[(3S, 4S)-4-(BOC-Nva-amino)-5-cyclohexyl-3-hydroxy-pentyl]-, m.p. 205°–208°, FAB 567

2-[(3S, 4S)-4-(BOC-N I e-amino)-5-cyclohexyl-3-hydroxy-pentyl]-, m.p. 208°–209°, FAB 581

2-[(2S, 3S)-3-(4-BOC-amino-piperidinocarbonyl-Phe-Met($O_2$)-amino)-4-cyclohexyl-2-hydroxy-butyl ]-, m.p. 186°–188°, FAB 891

2-[(3S, 4S)-4-(4-BOC-amino-piperidinocarbonyl-Phe-Nva-amino)-5-cyclohexyl-3-hydroxy-pentyl]-, m.p. 148° (decomposition), FAB 841

2-[(2S,3S)-3-(4-BOC-amino-piperidinocarbonyl-Pla-βAla-amino)-4-cyclohexyl-2-hydroxy-butyl]-, FAB 800

2-[(3S, 4S)-4-(4-BOC-amino-piperidinocarbonyl-Phe-Nle-amino)-5-cyclohexyl-3-hydroxy-pentyl]-, m.p. 176° (decomposition), FAB 855

2-[(3S, 4S)-4-BOC-Leu-Met-amino-5-cyclohexyl-3-hydroxypentyl]-, m.p. 167°–169°, FAB 712

2-[(3S, 4S)-4-(4-BOC-amino-piperidinocarbonyl-Pla-(S-Me-Cys)-amino)-5-cyclohexyl-3-hydroxy-pentyl]-, m.p. 176° (decomposition), FAB 860

2-[(3S, 4S)-4-(4-BOC-amino-piperidinocarbonyl-Pla-Nva-amino)-5-cyclohexyl-3-hydroxy-pentyl]-, m.p. 150° (decomposition), FAB 842

2-[(2S,3S)-3-(2-benzyl-3-tert.-butyl-sulfonyl-propionyl-Nva-amino)-4-cyclohexyl-2-hydroxy-butyl]-, 2 isomers, m.p. 132°–138° (decomposition) and m.p. 121°–127°, respectively, FAB 719 each 2-[(2S,3S)-3-(2-Benzyl-3-tert.-butyl-sulfonyl-propionyl-(S-He-Cys)-amino)-4-cyclohexyl-2-hydroxy-butyl]-, 2 isomers, FAB 737 and m.p. 204°–205°, FAB 737, respectively 2-[(2S, 1S)-3-BOC-Phe-(S-Ne-Cys )-amino-4-cyclohexyl-2-hydroxy-butyl]-, m.p. 215°–217°, FAB 718

2-[(2S, 3S)-3-(3-BOC-amino-3-methylbutyryl-Phe-(S-Ne-Cys)-amino)-4-cyclohexyl-2-hydroxy-butyl]-, m.p. 211°–212°, FAB 818

2-[(2S,1S)-3-(4-BOC-amino-piperidinocarbonyl-Pla-(S-Ne-Cys)-amino)-4-cyclohexyl-2-hydroxy-butyl ]-, m.p. 217°–219°, FAB 846

2-[(2S, 3S)-3-(3-phenylpropionyl-(S-Ne-Cys)-amino)-4-cyclohexyl-2-hydroxy-butyl ]-, m.p. 244°–246°, FAB 603

2-[(2S, 3S)-3-(4-BOC-amino-piperidinocarbonyl-Pla-Nle-amino)-4-cyclohexyl-2-hydroxy-butyl]-, m.p. 218°–219°, FAB 827

2-[(2S, 3S)-3-(3-phenylpropionyl-Nva-amino)-4-cyclohexyl-2-hydroxy-butyl]-, m.p. 252°–255°, FAB 585

2-[(3S, 4S)-4-(3-phenylpropionyl-(S-He-Cys)-amino)-5-cyclohexyl-3-hydroxy-pentyl]-, m.p. 192°–198° (decomposition), FAB 617

2-[(3S, 4S)-4-(3-pyridylacetyl-(S-He-Cys)-amino)-5-cyclohexyl-3-hydroxy-pentyl ]-, m.p. 159°–163°, FAB 604

2-[(3S, 4S)-4-(4-pyridylacetyl-(S-He-Cys)-amino)-5-cyclohexyl-3-hydroxy-pentyl]-, m.p. 206°–207°, FAB 604

2-[(3S, 4S)-4-(4-pyridylmercapto-acetyl-(S-He-Cys)-amino)-5-cyclohexyl-3-hydroxy-pentyl]-, m.p. 198°–204° (decomposition), FAB 636

2-[(3S, 4S)-4-(BOC-Het($O_2$)-(S-He-Cys)-amino)-5-cyclohexyl-3-hydroxy-pentyl]-, m.p. 202° (decomposition), FAB 748

2-[(3S, 4S)-4-(2-pyrimidinylmercapto-acetyl-(S-Ne-Cys)-amino)-5-cyclohexyl-3-hydroxy-pentyl]-, m.p. 198°–200°, FAB 637

2-[(3S, 4S)-4-(4-BOC-amino-piperidinocarbonyl-Phe-(S-He-Cys)-amino)-5-cyclohexyl-3-hydroxy-pentyl]-, m.p. 151°–162°, FAB 858

2-[(2S, 3S)-3-(4-BOC-amino-piperidinocarbonyl-Phe-Ser-amino)-4-cyclohexyl-2-hydroxy-butyl]-, m.p. 155°–158°, FAB 814

2-[(2S, 3S)-3-(4-morpholinocarbonyl-Phe-(S-Ne-Cys)-amino)-4-cyclohexyl-2-hydroxy-butyl]-, m.p. 178°–180°, FAB 731

2-[(2S, 3S)-3-(4-BOC-amino-piperidinocarbonyl-Phe-Isoser-amino)-4-cyclohexyl-2-hydroxy-butyl]-, 2 isomers, m.p. 135° and 145° respectively, FAB 8.14 each 2-[(3S, 4S)-4-(N-benzyl-N-methyl-carbamoyl-(S-He-Cys)-amino)-5-cyclohexyl-3-hydroxy-pentyl]-, m.p. 180° (decomposition), FAB 646

2-[(3S, 4S)-4-(2-benzyl-3-tert.-butylsulfonyl-propionylamino)-5-cyclohexyl-3-hydroxy-pentyl]-, 2 isomers, FAB 634 each 2-[(3S, 4S)-4-(2-pyridyl-acetyl-(S-He-Cys)-amino)-5-cyclohexyl-3-hydroxy-pentyl]-, m.p. 152°–157° (decomposition), FAB 604

2-[(3S, 4S)-4-(3-anilino-propionyl-(S-He-Cys)-amino)-5-cyclohexyl-3-hydroxy-pentyl]-, hydrochloride, m.p. 148°(decomposition), FAB 633

2-[(3S, 4S)-4-(3-phenylpropionyl-Nva-amino)-5-cyclohexyl-3-hydroxy-pentyl]-, m.p. 198°–201 °, FAB 600

2-[(3S, 4S)-4-(2-pyridylacetyl-Nva-amino)-5-cyclohexyl-3-hydroxy-pentyl]-, m.p. 130° (decomposition), FAB 586

2-[(3S, 4S)-4-(3-pyridylacetyl-Nva-amino)-5-cyclohexyl-3-hydroxy-pentyl]-, m.p. 208° (decomposition), FAB 586

2-[(3S, 4S)-4-(4-pyridylacetyl-Nva-amino)-5-cyclohexyl-3- hydroxy-pentyl]-, m.p. 138° (decomposition), FAB 586

2-[(3S, 4S)-4-(4-pyridylmercaptoacetyl-Nva-amino)-5-cyclohexyl-3-hydroxy-pentyl]-, m.p. 181°(decomposition), FAB 618

2-[(3S, 4S)-4-(N-benzyl-N-methyl-Gly-Nva-amino)-5-cyclohexyl-3-hydroxy-pentyl]-, m.p. 198° (decomposition), FAB 628

2-[(3S, 4S)-4-(2-pyrimidinyl-mercapto-acetyl-Nva-amino)-5-cyclohexyl-3-hydroxy-pentyl ]-, m.p. 183° (decomposition), FAB 619

2-[(3S, 4S)-4-(3-anilinopropionyl-Nva-amino)-5-cyclohexyl-3-hydroxy-pentyl]-, m.p. 170°–172° , FAB 614

2-[(4S, 5S)-5-(2-benzyl-3-tert.-butylsulfonyl-propionylamino)-6-cyclohexyl-4-hydroxy-hexyl]-, 2 isomers, m.p. 218°–220° and 182°–184°, respectively, FAB 648 each 2-[(4S, 5S)-5-(BOC-Phe-(S-Ne-Cys)-amino)-6-cyclohexyl-4-hydroxy-hexyl]-, m.p. 193°–195°, FAB 746

2-[(2S, 3S)-3-(2-benzyl-3-tert.-butylsulfonyl-propionylamino)-4-cyclohexyl-2-hydroxy-butyl]-, 2 isomers, m.p. 170°–171° and 230°–233°, respectively, FAB 620 each 2-[(4S, 5S)-5-(2-benzyl-3-tert.-butylsulfonyl-propionyl-Nle-amino)-6-cyclohexyl-4-hydroxy-hexyl]-, 2 isomers, m.p. 122°–124° (decomposition) and 218°–221° (decomposition), respectively, FAB 761 each 2-[(4S, 5S)-5-(3-BOC-amino-3-methyl-butyryl-amino)-6-cyclohexyl-4-hydroxy-butyl]-, m.p. 91° (decomposition), FAB 581

2-[(4S, 5S)-5-(3-BOC-amino-3-methyl-butyryl-Nva-amino)-6-cyclohexyl-4-hydroxy-butyl]-, m.p. 168°–171° (decomposition), FAB 680

2-[(4S, 5S)-5-(2-benzyl-3-tert.-butylsulfonyl-propionyl-(S-Me-Cys)-amino)-6-cyclohexyl-4-hydroxy-hexyl]-, 2 isomers, m.p. 222°–223° and 111°–113°, FAB 765 each 2-[(4S, 5S)-5-(4-BOC-amino-piperidinocarbonyl-Phe-βAla-amino)-6-cyclohexyl-4-hydroxy-hexyl]-, m.p. 128°–130°, FAB 826

2-[(4S, 5S)-5-(2-benzyl-3-tert.-butylsulfonyl-propionyl-Nva-amino)-6-cyclohexyl-4-hydroxy-hexyl]-, FAB 761

2-[(2S,1S)-3-(BOC-(S-Me-Cys)-(S-Me-Cys)-amino)-4-cyclohexyl-2-hydroxy-butyl]-, m.p. 201°–

2-[(4S, 5S)-5-(4-BOC-amino-piperidinocarbonyl-Phe-Nva-amino)-6-cyclohexyl-4-hydroxy-hexyl]-, m.p. 134°–139°, FAB 854

2-[(4S, 5S)-5-(4-BOC-amino-piperidinocarbonyl-Phe-Nle-amino)-6-cyclohexyl-4-hydroxy-hexyl]-, m.p. 135°–140°, FAB 868

2-[(2S,3S)-3-(4-phenyl-4-piperidinylcarbonyl-(S-Me-Cys)amino)-4-cyclohexyl-2-hydroxy-butyl]-, m.p. 163°–166° (decomposition), FAB 658

2-[(3S, 4S)-4-(BOC-Ser-(S-Me-Cys)-amino)-5-cyclohexyl-3-hydroxy-pentyl]-, m.p. 114° (decomposition)

2-[(3S, 4S)-4-(4-phenyl-2-pyridyl-carbonyl-(S-Me-Cys)-amino)-5-cyclohexyl-3-hydroxy-pentyl]-, hydrochloride, m.p. 153° (decomposition), FAB 666

2-[(3S, 4S)-4-(4-phenyl-3-pyridyl-carbonyl-(S-Me-Cys)-amino)-5-cyclohexyl-3-hydroxy-pentyl]-, hydrochloride, m.p. 158° (decomposition), FAB 666

2-[(3S, 4S)-4-(5-p-fluorophenyl-3-pyridyl-carbonyl-(S-Me-Cys)-amino)-5-cyclohexyl-3-hydroxy-pentyl]-, hydrochloride, FAB 685

2-[(2S,3S)-3-(phenylacetyl-(S-He-Cys)-amino)-4-cyclohexyl-2-hydroxy-butyl]-, m.p. 237°–239°, FAB 589

2-[(3S, 4S)-4-(4-BOC-amino-piperidinocarbonyl-Phe-Thr-amino)-5-cyclohexyl-3-hydroxy-pentyl]-, m.p. 138°–146° (decomposition), FAB 842.

Example 21

In analogy to Example 12, the following 1,3-dithiane 1,1,3,3-tetroxides are obtained from the corresponding BOC-amino derivatives:

2-[(3S, 4S)-4-(4-amino-piperidinocarbonyl-Phe-βAla-amino)-5-cyclohexyl-3-hydroxy-pentyl]-, m.p. 187° (decomposition), FAB 712

2-[(3S, 4S)-4-(4-amino-piperidinocarbonyl-Phe-amino)-5-cyclohexyl-3-hydroxy-pentyl]-, m.p. 164° (decomposition), FAB 641

2-[(3S, 4S)-4-(4-piperidylcarbonyl-amino)-5-cyclohexyl-3-hydroxy-pentyl]-, m.p. 167° (decomposition), FAB 479

2-[(2S, 3S)-3-(4-piperidylcarbonyl-amino)-4-cyclohexyl-3-hydroxy-butyl]-, m.p. 244° (decomposition), FAB 465

2-[(3S, 4S)-4-(4-amino-piperidinocarbonyl-Phe-Gln-amino)-5-cyclohexyl-3-hydroxy-pentyl]-, m.p. 193° (decomposition), FAB 769

2-[(3S, 4S)-4-(4-amino-piperidinocarbonyl-Phe-Asn-amino)-5-cyclohexyl-3-hydroxy-pentyl]-, m.p. 198° (decomposition), FAB 755

2-[(3S, 4S)-4-(H-Nle-amino)-5-cyclohexyl-3-hydroxy-pentyl]-, m.p. 180° (decomposition), FAB 481

2-[(2S, 3S)-3-(4-amino-piperidinocarbonyl-Phe-(S-Me-Cys)-amino)-4-cyclohexyl-2-hydroxy-butyl]-, m.p. 142°–145°, FAB 745

2-[(2S,3S)-3-(4-amino-piperidinocarbonyl-Pla-His-amino)-4-cyclohexyl-2-hydroxy-butyl]-, m.p. 130°–133°, FAB 766

2-[(3S, 4S)-4-(4-amino-piperidinocarbonyl-Phe-Nva-amino)-5-cyclohexyl-3-hydroxy-pentyl]-, m.p. 192° (decomposition), FAB 740

2-[(2S, 3S)-3-(4-amino-piperidinocarbonyl-Phe-Met-amino)-4-cyclohexyl-2-hydroxy-butyl]-, m.p. 175° (decomposition), FAB 758

2-[(2S, 3S)-3-(4-amino-piperidinocarbonyl-Phe-Het-(O₂)-amino)-4-cyclohexyl-2-hydroxy-butyl]-, m.p. 198° (decomposition), FAB 790

2-[(2S, 3S)-3-(4-amino-piperidinocarbonyl-Pla-βAla-amino)-4-cyclohexyl-2-hydroxy-butyl]-, FAB 699

2-[(3S, 4S)-4-(4-amino-piperidinocarbonyl-Phe-Nle-amino)-5-cyclohexyl-3-hydroxy-pentyl]-, m.p. 178° (decomposition), FAB 754

2-[(3S, 4S)-4-(4-amino-piperidinocarbonyl-Pla-(S-Me-Cys)-amino)-5-cyclohexyl-3-hydroxy-pentyl]-, FAB 759

2-[(2S, 3S)-3-H-Phe-(S-Me-Cys)-amino-4-cyclohexyl-2-hydroxybutyl]-, m.p. 208°–210°, FAB 618

2-[(3S, 4S)-4-(4-amino-piperidinocarbonyl-Pla-Nva-amino)-5-cyclohexyl-3-hydroxy-pentyl]-, m.p. 176° (decomposition). FAB 741

2-[(3S, 4S)-4-(H-Met(O₂)-(S-Me-Cys)-amino)-5-cyclohexyl-3-hydroxy-pentyl]-, m.p. 153° (decomposition), FAB 648

2-[(3S, 4S)-4-(4-amino-piperidinocarbonyl-Phe-(S-Me-Cys)-amino)-5-cyclohexyl-3-hydroxy-pentyl]-, m.p. 172° (decomposition), FAB 758

2-[(2S, 3S)-3-(3-amino-3-methyl-butyryl-Phe-(S-Me-Cys)-amino)-4-cyclohexyl-2-hydroxy-butyl]-, m.p. 172°–175°. FAB 717

2-[(2S, 3S)-3-(4-amino-piperidinocarbonyl-Phe-Met-amino)-4-cyclohexyl-2-hydroxy-butyl ]-, hydrochloride, m.p. 185° (decomposition), FAB 758

2-[(2S, 3S)-3-(4-amino-piperidinocarbonyl-Phe-Ser-amino)-4-cyclohexyl-2-hydroxy-butyl]-, hydrochloride, m.p. 194° (decomposition), FAB 714

2-[(2S,3S)-3-(4-amino-piperidinocarbonyl-Pla-(S-Me-Cys)-amino-4-cyclohexyl-2-hydroxy-butyl ]-, hydrochloride, m.p. 220° (decomposition), FAB 745

2-[(2S, 3S)-3-(4-amino-piperidinocarbonyl-Pla-Nva-amino)-4-cyclohexyl-2-hydroxy-butyl]-, hydrochloride, m.p. 215° (decomposition), FAB 727

2-[(4S, 5S)-5-(4-amino-piperidinocarbonyl-Phe-Hle-amino)-6-cyclohexyl-4-hydroxy-hexyl]-, trifluoroacetate, m.p. 138°–139°, FAB 768

2-[(4S, 5S)-5-(4-amino-piperidinocarbonyl-Phe-Hva-amino)-6-cyclohexyl-4-hydroxy-hexyl]-, trifluoroacetate, m.p. 133°–135°, FAB 754

2-[(2S,3S)-3-(4-amino-piperidinocarbonyl-Pla-His-amino)-4-cyclohexyl-2-hydroxy-butyl]-, dihydrochloride, m.p. 216°, FAB 765.

Example 22

In analogy to Example 6, 2-[(1S,2S)-2-BOC-amino-3-cyclohexyl-1-hydroxy-propyl]-1,3-dithiane, FAB 376, is obtained from (4S,5S)-3-BOC-4-cyclohexylmethyl-2,2-dimethyl-5-oxazolidinyl-carbaldehyde and 1,3-propanedithiol.

Example 23

A mixture of 1 g of 2-[(-1S,2S)-2-BOC-amino-3-cyclohexyl-1-hydroxy-propyl-1,3-dithiane, 5 ml of 2,2-dimethoxypropane, 0.1 g of p-toluenesulfonic acid and 50 ml of dichloromethane is stirred for 16 hours at 20°. The mixture is extracted with NaHCO₃ solution, washed neutral and evaporated. 2-[(4S,5S)-3-BOC-4- cyclohexylmethyl-2,2-dimethyl-5-oxazolidinyl]-1,3-dithiane is obtained.

Example 24

A 1.6 molar solution. (1.7 ml) of butyllithium in hexane is added under a N₂ atmosphere at −40° to a solution of 0.51 g of 2-[2-((4S,5S)-3-BOC-4-cyclohexylmethyl-2,2-dimethyl-5-oxazolidinyl]-ethyl]-1,3-dithiane 1,1,3,3-tetroxide in 15 ml of THF. After 1 hour stirring, 0.26 ml of ethyl 3-bromopropionate is added, the mixture is stirred for 1 hour at −40° and for 24 hours at 25° and worked up in the usual manner (water/diethyl ether). 2-[2-((4S,5S)-3-BOC-4-cyclohexylmethyl-2,2-dimethyl-5-oxazolidinyl )-ethyl/-2-(2-ethoxycarbonylethyl)-1,3-dithiane 1,1,3,3-tetroxide, m.p. 160°–161°, FAB 608, is obtained.

The examples which follow relate to pharmaceutical compositions:

Example A: Tablets

A mixture of 1 kg of 2-[(2S,3S)-3-BOC-Phe-His-amino-4-cyclohexyl-2-hydroxybutyl]-1,3-dithiane 1,1,3,3-tetroxide, 4 kg of lactose, 1.2 kg of maize starch, 200 g of talc and 100 g of magnesium stearate is compressed in a customary manner to give tablets in such a way that each tablet contains 100 mg of active compound.

Example B: Coated tablets

Tablets are compressed in analogy to Example A and are then coated in a customary manner with a coating composed of sucrose, maize starch, talc, tragacanth and colorant.

Example C: Capsules 500 g of 2-[(2S,3S)-3-(4-aminopiperidinocarbonyl-Phe-His-amino)-4-cyclohexyl-2-hydroxybutyl]-1,3-dithiane 1,1,3,3-tetroxide are dispensed in a customary manner into hard gelatine capsules so that each capsule contains 500 mg of active compound.

Example D: Injection ampoules

A solution of 100 g of 2-[(2S,3S)-3-(4-aminopiperidinocarbonyl-Phe-His-amino)-4-cyclohexyl-2-hydroxybutyl]-1,3-dithiane 1,1,3,3-tetroxide in 4 l of double-distilled water is adjusted to pH 6.5 with 2N hydrochloric acid, filtered sterile and dispensed into injection ampoules. These are lyophilized under sterile conditions and sealed sterile. Each injection ampoule contains 50 mg of active compound.

Example E: Suppositories

A mixture of 50 g of 2-[(2S,3S)-3-(4-BOC-amino-piperidinocarbonyl-Phe-amino)-4 -cyclohexyl-2-hydroxybutyl]-1,3-dithiane 1,1,3,3-tetroxide with 10 g of soya lecithin and 140 g of cocoa butter is melted, poured into moulds and left to cool. Each suppository contains 250 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,3-dithiane compound of formula I $$R^1-Z-NR^2-CHR^3-CR^4-(CH_2)_o-CE-R^6$$

in which
R¹ is A—O—CO—, A—SO₂—CH₂—CH(CH₂—C₆H₅)—CO—, 4-A—O—CO—NH—piperidinocarbonyl, 4-amino-piperidinocarbonyl, A—O—CO—NH—C(CH₃)₂—CH₂—CO—, H₂N—C(CH₃)₂—CH₂—CO— or morpholinocarbonyl;

Z is 1 or 2 amino acid residues which are linked together in the manner of a peptide and are selected from the group consisting of βAla, Cal, S-A-Cys, Gln, His, Leu, Mal, Met, Met(O)₂, Nle, Nva, Phe, Ser, Thr and Val, wherein one of these radicals may also be replaced by Pla;

R² is H;
R³ is cyclohexylmethyl;
R⁴ is (H,OH);
o is 1, 2, 3 or 4;
E is —S—(CH₂)₃— or —SO₂—(CH₂)₃—SO₂—;
R⁶ is H or A; and
A is alkyl or 1–4 carbon atoms; or
an acid addition salt thereof.

2. A compound according to claim 1, wherein said compound is
 a) 2-[(2S,3S)-3-(BOC-Phe-His-amino)-4-cyclohexyl-2-hydroxy-butyl]-1,3-dithiane; or
 b) 2-[(2S,3S)-3-(BOC-Phe-His-amino)-4-cyclohexyl-2-hydroxy-butyl]-1,3-dithiane 1,1,3,3-tetroxide.

3. A compound according to claim 1, wherein
R¹ is BOC, 2-benzyl-3-tert-butylsulfonyl-propionyl, 4-BOC-amino-piperidinocarbonyl, 4-amino-piperidinocarbonyl, 3-BOC-amino-3-methyl-butyryl, 3-amino-3-methyl-butyryl or morpholinocarbonyl;

Z is S-Me-Cys, His, Nle, Nva, (S-Me-Cys)-(S-Me-Cys), Mal-His, Phe-βAla, Phe-Gln, Phe-His, Phe-Leu, Phe-(S-Me-Cys), Phe-Met, Phe-Met(O)₂, Phe-Nle, Phe-Nva, Phe-Ser, Phe-Thr, Phe-Val, Pla-(S-Me-Cys), Pla-His, Pla-Met, Pla-Nle or Pla-Nva; and R⁶ is H or methyl; or
an acid addition salt thereof.

4. A compound according to claim 3, wherein
Z is S-Me-Cys, His, Phe-(S-Me-Cys), Phe-His, Phe-Met, Phe-Nva, Pla-(S-Me-Cys) or Pla-His; or
an acid addition salt thereof.

5. A compound according to claim 1, wherein
R⁶ is H or CH₃.

6. A compound according to claim 1, wherein
Z is His, Nva, Nle, Phe-His, Phe-Leu, Mal-His, Phe-βAla, Phe-Nva, Phe-Gln, Phe-Val, Phe-Met, Phe-(S-Me-Cys), Pla-His, Phe-Met(O)₂), Phe-Nle, (S-Me-Cys), Pla-(S-Me-Cys), Phe-Ser, Pla-Nle, Pla-Nva, Phe-Thr, or Pla-Met.

7. A compound according to claim 1, wherein
E is —S—(CH₂)₃—S—.

8. A compound according to claim 1, wherein
E is —SO₂—(CH₂)₃—SO₂—.

9. A compound according to claim 1, wherein
o is 1, 2 or 3.

10. A 1,3-dithiane compound according to claim 1, wherein o is 2, 3, or 4.

11. A compound according to claim 1, wherein
Z is His, Leu, Mal-His, Phe-His or Phe-Leu, and $R^6$ is H or $CH_3$.

12. A compound according to claim 1, wherein
   $R^1$ is BOC, 4-BOC-amino-piperidinocarbonyl or 4-amino-piperidinocarbonyl,
   Z is Phe-His or Phe-Leu,
   E is $-SO_2-(CH_2)_3-SO_2-$ and
   $R^6$ is H.

13. A pharmaceutical composition comprising a compound of claim 1 and a pharmaceutically acceptable carrier.

14. A pharmaceutical composition according to claim 13, wherein said composition comprises about 10 mg–1 g of a compound of claim 1.

15. A method of treating renin-dependent hypertension or renin-dependent hyperaldosteronism comprising administering a compound of claim 1.

16. A method according to claim 15, comprising administering doses of said compound in an amount of 0.2–20 mg/kg of body weight.

17. A method of treating or prophylaxis of renin-dependent hypertension, renin-dependent cardiac insufficiency, or renin-dependent hyperaldosteronism comprising administering a compound of claim 1.

18. A method according to claim 17, comprising administering said compound in an amount of about 0.2–20 mg/kg of body weight.

* * * * *

UNITED STATES PATENT AND TRADEMARK OFFICE
CERTIFICATE OF CORRECTION

PATENT NO. : 5,401,722
DATED : March 28, 1995
INVENTOR(S) : Horst JURASZYK et al.

It is certified that error appears in the above-indentified patent and that said Letters Patent is hereby corrected as shown below:

Title page; Item [76] Inventors: After the first inventor's name insert - - Seeheim; - -.

Title page; Item [76] Inventors: Following the third inventor's name insert - - both of Darmstadt; - -.

Title page; Item [76] Inventors: After the fourth inventor's name insert - - Gross-Umstadt; - -.

Title page; Item [76] Inventors: After the fifth inventor's name insert - -Ober-Ramstadt; - -.

Title page; Item [76] Inventors: Delete "10".

Title page: After Item [76] and before Item [21], Insert name of assignee as follows:
- - Item [73] MERCK PATENT GESELLSCHAFT MIT BESCHRANKTER HAFTUNG, DARMSTADT, GERMANY - -.

Signed and Sealed this

Twenty-ninth Day of August, 1995

Attest:

BRUCE LEHMAN

*Attesting Officer*    *Commissioner of Patents and Trademarks*